US007579164B2

(12) United States Patent
Bender et al.

(10) Patent No.: US 7,579,164 B2
(45) Date of Patent: Aug. 25, 2009

(54) **OPTIMIZATION OF CORONATINE PRODUCTION IN A GENETICALLY IMPROVED STRAIN OF *PSEUDOMONAS SYRINGAE***

(75) Inventors: Carol L. Bender, Stillwater, OK (US); Alejandro Penaloza-Vazquez, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 0 days.

(21) Appl. No.: 11/740,029

(22) Filed: Apr. 25, 2007

(65) Prior Publication Data

US 2007/0264691 A1 Nov. 15, 2007

Related U.S. Application Data

(60) Provisional application No. 60/795,474, filed on Apr. 27, 2006, provisional application No. 60/795,475, filed on Apr. 27, 2006.

(51) Int. Cl.
*C12P 1/00* (2006.01)

(52) U.S. Cl. .................................. 435/41; 435/440

(58) Field of Classification Search .................. 435/41, 435/440

See application file for complete search history.

(56) References Cited

U.S. PATENT DOCUMENTS

| | | | | |
|---|---|---|---|---|
| 5,397,697 | A * | 3/1995 | Lam et al. | 435/6 |
| 6,428,989 | B1 * | 8/2002 | Yukimune et al. | 435/123 |
| 6,511,939 | B1 | 1/2003 | Burns et al. | |
| 2003/0013609 | A1 | 1/2003 | Burns et al. | |
| 2003/0175913 | A1 | 9/2003 | Steele et al. | |

OTHER PUBLICATIONS

Penaloza-Vazquez et al. 2000; Regulatory interactions between the Hrp type III protein secretion system and coronatine biosynthesis in *Pseudomonas syringae* pv. *tomato* DC3000. Microbiology 146: 2447-2456.*

Rohmer et al. Mar. 2003; Nucleotide sequence, functional characterization and evolution of pFKN, a virulence plasmid in *Pseudomonas syringae* pathovar *maculicola*. Molecular Microbiology 47(6): 1545-1562.*

Landgraf 2006; Different versions of *Pseudomonas syringae* pv. *tomato* DC3000 exist due to the activity of an effector transposon. Molecular Plant Pathology 7(5): 355-364.*

Alarcon-Chaidez et al., Characterization of Plasmids Encoding the Phytotoxin Coronatine in *Pseudomonas syringae, Plasmid*, 1999, pp. 210-220, vol. 42, Publisher: Academic Press.

Bender et al., *Pseudomnas syringae* Phytotoxins: Mode of Action, Regulation, and Biosynthesis by Peptide and Polyketide Synthetases, *Microbiology and Molecular Biology Reviews*, 1999, pp. 266-292, vol. 63, No. 2, Publisher: American Society for Microbiology.

Bender et al., Characterization of the genes controlling the biocynthesis of the polyketide phytotoxin coronatine including conjugation between coronafacis and coronamic acid, *Gene*, 1993, pp. 31-38, vol. 133, Publisher: Elsevier Science Publishers.

Bender et al., Polyketide Production by Plant-Associated *Pseudomonads*, www.annualreviews.org.

Bender et al., Conservation of Plasmid DNA Sequences in Coronatine-Producing Pathovars of *Pseudomonas syringae, Applied and Environmental Microbiology*, 1991, pp. 993-999, vol. 57, No. 4, Publisher: American Society for Microbiology.

Bereswill et al., Identification and Relatedness of Coronatine-Producing *Pseudomonas syringae* Pathovars by PCR Analysis and Sequence Determination of the Amplification Products, *Applied and Environmental Microbiology*, 1994, pp. 2924-2930, vol. 60, No. 8, Publisher: American Society for Microbiology.

Budde et al., Growth Phase and Temperature Influence Promoter Activity, Transcript Abundance, and Protein Stability during Biosynthesis of the *Pseudomonas syringae* Phytotoxin Coronatine, *Journal of Bacteriology*, 1998, pp. 1360-1367, vol. 180, No. 6, Publisher: American Society for Microbiology.

Feys et al., *Arabidopsis* Mutants Selected for Resistance to the Phytotoxin Coronatine are Male Sterile, Insensitive to Methyl Jasmonate, and Resistant to a Bacterial Pathogen, *The Plant Cell*, 1994, pp. 751-759, vol. 6, Publisher: American Society of Plant Physiologists.

Hirano et al., Bacteria in the Leaf Ecosystem with Emphasis on *Pseudomonas syringae*—a Pathogen, Ice Nucleus, and Epiphyte, *Microbiology and Molecular Biology Reviews*, 2000, pp. 624-653, vol. 64, No. 3, Publisher: American Society for Microbiology.

Hrabak et al., The lemA gene required for pathogenicity of *Pseudomnas syringae* pv. *syringae* on bean is a member of a family of two-component regulatros, *Journal of Bacteriology*, 1992, pp. 3011-3020, vol. 174, No. 9, Publisher: American Society for Microbiology.

Jiralerspong et al., Analysis of the enzymatic domains in the modular portion of the coronafacic acid polyketide snythase, *Gene*, 2001, pp. 191-200, vol. 270, Publisher: Elsevier Science.

Keith et al., AlgT($\delta^{22}$) Controls Alginate Production and Tolerance to Environmental Stress in *Pseudomonas syringae, Journal of Bacteriology*, 1999, pp. 7176-7184, vol. 181, No. 23, Publisher: American Society for Microbiology.

(Continued)

*Primary Examiner*—Karen Cochrane Carlson
(74) *Attorney, Agent, or Firm*—Fellers, Snider, Blankenship, Bailey & Tippens, PC

(57) ABSTRACT

Stable genetically engineered bacterial strains that overproduce coronatine are provided. The stable strains can be successfully cultivated to overproduce coronatine at temperatures that are suitable for large scale, commercial preparations of coronatine. The overproducing strains are also non-pathogenic. An exemplary strain is *Pseudomonas syringae* APV1, which successfully overproduces coronatine at 26° C. Methods of optimizing culture conditions for coronatine production from the novel stable overproducing strains are provided, as are methods for using the overproducing strains to induce abscission and increase taxane production.

25 Claims, 11 Drawing Sheets

OTHER PUBLICATIONS

Liyanage et al., Characterization and Transcriptional Analysis of the Gene Cluster for Coronafacic Acid, the Polyketide Component of the Phytotoxin Coronatine, *Applied and Environmental Microbiology*, 1995, pp. 3843-3848, Publisher: American Society for Microbiology.

Liyanage et al., Sequence, expression and transcriptional analysis of the coronafacate ligase-encoding gene required for coronatine biosynthesis by *Pseudomonas syringae, Gene*, 1995, pp. 17-23, vol. 153, Publisher: Elsevier Science.

Palmer et al., Effects of Environmental and Nutritional Factors on Production of the Polyketide Phytotoxin Coronatine by *Pseudomonas syringae* pv. *Glycinea, Applied and Environmental Microbiology*, 1993, pp. 1619-1626, vol. 59, No. 5, Publisher: American Society for Microbiology.

Penaloza-Vasquez et al., Characterization of CorR, a Transcriptional Activator Which Is Required for Biosynthesis of the Phytotoxin Coronatine, *Journal of Bacteriology*, 1998, pp. 6252-6259, vol. 180, No. 23, Publisher: American Society for Microbiology.

Penfold et al., Characterisation of genes involved in biosynthesis of coronafacic acid, the polyketide component of the phytotoxin coronatine, *Gene*, 1996, pp. 167-173, vol. 183, Publisher: Elsevier.

Rangaswamy et al., Biosynthesis of the *Pseudomonas* polyketide coronafacic acid requires monofunctional and multifunctional polyketide synthase proteins, *Proc. Natl. Acad. Sci. USA*, 1998, pp. 15469-15474, vol. 95, Publisher: The National Academy of Sciences.

Rangaswamy et al., Analysis of Genes Involved in Biosynthesis of Coronafacic Acid, the Polyketide Component of the Phytotoxin Coronatine, *Journal of Bacteriology*, 1998, pp. 3330-3338, vol. 180, No. 13, Publisher: American Society for Microbiology.

Rich et al., Pathovar-specific requirement for the *Pseudomonas syringae* lemA gene in disease lesion formation, *Applied and Environmental Microbiology*, 1992, pp. 1440-1446, vol. 58, No. 5.

Rich et al., Genetic evidence that the gacA gene encodes the cognate response regulator for the lemA sensor in *Pseudomonas syrinage, Journal of Bacteriology*, 1994, pp. 7468-7475, vol. 176, No. 24, Publisher: American Soceity for Microbiology.

Ullrich et al., The Biosynthesis Gene Cluster for Coronamic Acid, an Ethylcyclopropyl Amino Acid, Contains Genes Homologous to Amino Activating Enzymes and Thioesterases, *Journal of Bacteriology*, 1994, pp. 7574-7586, vol. 176, No. 24, Publisher: American Society for Microbiology.

Ullrich et al., Cloning Expression of Genes Required for Coronamic Acid (2-Ethyl-1-Aminocyclopropane 1-Carboxylic Acid), an Intermediate in the biosynthesis of the Phytotoxin Coronatine, *Applied and Environmental Microbiology*, 1994, pp. 2890-2897, vol. 60, No. 8, Publisher: American Society for Microbiology.

Ullrich et al., A Modified Two-Component Regulatory System is Involved in Temperature-Dependent Biosynthesis on the *Pseudomonas syringae* Phytotoxin Coronatine, *Journal of Bacteriology*, 1995, pp. 6160-6169, vol. 177, No. 21, Publisher: American Society for Microbiology.

Whistler et al., The Two-Component Regulators GacS and GacA Influence Accumulation of the Stationary-Phase Sigma Factor $\delta^S$ and the Stress Response in *Pseudomonas fluorescens* Pf-5, *Journal of Bacteriology*, 1998, pp. 6635-6641, vol. 180, No. 24, Publisher: American Society for Microbiology.

Young et al., Physical and Functional Characterization of the Gene Cluster Encoding the Polyketide Phytotoxin Coronatine in *Pseudomonas syringae* pv. *glycinea, Journal of Bacteriology*, 1992, pp. 1837-1843, vol. 174, No. 6, Publisher: American Society for Microbiology.

De Lorenzo, et al., "Mini-Tn5 Transposon Derivatives for Insertion Mutagenesis, Promoter Proving, and Chromosomal Insertion of Cloned DNA in Gram-Negative Eubacteria", "Journal of Bacteriology", Aug. 16, 1990, pp. 6568-6572, vol. 172, No. 11, Publisher: American Society for Microbiology, published in: US.

Rohde, et al., "Occurance of thermoregulation of genes involved in coronatine biosynthesis among various *Pseudomonas syringae* straings", "J. Basic Microbiol.", Nov. 12, 1997, pp. 1, 41-50, vol. 38, Published in: US.

U.S. Appl. No. 10/751,297, by Carol Lavane Bender, et al. "Clones Containing Coronatine Gene Cluster, Transconjugates Thereof, and Methods of Producing Coronatine," filed Dec. 15, 2003, (Now Abondoned).

* cited by examiner

Coronafacic Acid (CFA)

Coronamic Acid (CMA)

L-alloisoleucine

L-isoleucine

Coronatine (COR)

CFA-aile

CFA-ile

A. $Km^R$ gene, nucleotide sequence

ATGATTGAACAAGATGGATTGCACGCAGGTTCTCCGGCCGCTTGGGTGGAGAGGCTATTCGGCTATGACTGGGCACA
ACAGACAATCGGCTGCTCTGATGCCGCCGTGTTCCGGCTGTCAGCGCAGGGGCGCCCGGTTCTTTTTGTCAAGACCG
ACCTGTCCGGTGCCCTGAATGAACTCCAAGACGAGGCAGCGCGGCTATCGTGGCTGGCCACGACGGGCGTTCCTTGC
GCAGCTGTGCTCGACGTTGTCACTGAAGCGGGAAGGGACTGGCTGCTATTGGGCGAAGTGCCGGGGCAGGATCTCCT
GTCATCTCACCTTGCTCCTGCCGAGAAAGTATCCATCATGGCTGATGCAATGCGGCGGCTGCATACGCTTGATCCGG
CTACCTGCCCATTCGACCACCAAGCGAAACATCGCATCGAGCGAGCACGTACTCGGATGGAAGCCGGTCTTGTCGAT
CAGGATGATCTGGACGAAGAGCATCAGGGGCTCGCGCCAGCCGAACTGTTCGCCAGGCTCAAGGCGCGGATGCCCGA
CGGCGAGGATCTCGTCGTGACCCATGGCGATGCCTGCTTGCCGAATATCATGGTGGAAAATGGCCGCTTTTCTGGAT
TCATCGACTGTGGCCGGCTGGGTGTGGCGGACCGCTATCAGGACATAGCGTTGGCTACCCGTGATATTGCTGAAGAG
CTTGGCGGCGAATGGGCTGACCGCTTCCTCGTGCTTTACGGTATCGCCGCTCCCGATTCGCAGCGCATCGCCTTCTA
TCGCCTTCTTGACGAGTTCTTCTGA

Figure 10A

B. *hrcC* gene, nucleotide sequence

ATGTCGCTCGACATGTCGCCTGTCCAGGGCAAGCTCGATGGCCGTATTCGTGCTCAGAACCCTGAAGAGTTTCTTGA
GCGGCTGAGTCAGGAATACCACTTCCAGTGGTTCGTCTATAACGACACGCTGTATGTCAGCCCTTCCAGCGAGCACA
CCTCGGCGCGCATCGAAGTCTCGCCGGATGCGGTGGACGACCTGCAAACGGCGCTGACCGATGTCGGTCTGCTGGAC
AAGCGTTTTGGCTGGGGCTCGCTGCCTGACGAAGGCGTGGTTCTGGTTCGTGGTCCGGCCAAATACGTGGAGTTTGT
GCGCGACTACAGCAAGAAAGTCGAAAAGCCCGACGAGAAGGCCGACAAGCAAGATGTTGTCGTGCTGCCACTCAAAT
ACGCCAACGCGGCTGATCGGACTATTCGCTACCGTGACCAGCAGTTAGTGGTGGCCGGTGTCGCCAGTATTCTTCAA
GAGCTGCTGGAAAGCCGTTCGCGTGGCGAAAGCATTGACAGCGTGAACCTGTTGCCGGGGCAGGGCAGCAGTGTTGC
CAACAGCACAGGTGTCGCGGCCGCCGGCCTGCCTTACAACCTGGGCTCCAATGGTATCGATACGGGAGCACTGCAAC
AGGGCATTGACCGCGTATTGAACTTCAACAGCAAAAAAACTGCCAAGGGTCATGCCTCAGGCAAGGCAAATATCCGC
GTAAGCGCTGATGTGCGTAACAACTCCGTATTGATTTACGACCTGCCAGAGCGCAAGGCCATGTACCAGAAACTGGT
CAAGGAGCTGGACGTTCCGCGCAACCTGATCGAAATCGATGCGGTCATTCTCGACATCGACCGCAATGAACTGGCTG
AACTGTCCAGTCGCTGGAATTTCAATGCCGGCAGCGTCGGAGGTGGTGCCAACCTGTTTGATGCAGGCACCAGTTCA
ACGTTGTTCTTGCAGAACGCCAGCAAGTTTTCTGCCGAATTGCATGCGCTTGAAGGCAATGGTTCTGCGTCAGTCAT
CGGCAACCCGTCGATCCTGACCCTGGAGAATCAGCCTGCAGTGATCGACCTCAGTCGCACCGAATACCTGACGGCCA
CTTCCGAGCGGGCCGCTGACATTCTGCCCATCACGGCGGGCACCAGCCTTCAAGTGATTCCGCGTTCGCTGGACAAC
GATGGCAAGCCTCAGGTGCAAATGATCGTGGACATCGAGGATGGCCAGATCGATGTGTCGACGATCAATGACACCCA
ACCCAGTGTGCGCCGAGGCAATGTCAGCACCCAGGCGGTGATTGCCGAGCACGGCTCGCTGGTCATCGGCGGCTTCC
ACGGTCTGGAAGCCAATGACAGGATTCACAAGATCCCGCTGTTGGGCGACATTCCCTATATCGGCAAGCTGCTGTTC
CAGTCCCGCAGTCGCGAACTGAGTCAGCGCGAGCGGCTGTTCATTCTGACCCCTCGACTGATCGGCGATCAGGTCAA
TCCAGCACGCTATGTACAGAACGGCAACCCCCATGACGTCGATGACCAGATGAAGAAAATCAAGGAACGACGTGACG
GAGGCGAGCTGCCAACGCGGGGCGACATCCAGAAAGTCTTTACCCAAATGATCGACGGCGCCGCCCCGGAAGGCCTG
CGCGCTGGCCAGACCCTGCCCTTTGAAACCGATAGTCTGTGTGATCCGGGCGAAGGTCTGACGCTTGATGGGCAGCG
CTCGCAGTGGTTCGTCAAAAAAGACTGGGGTGTTGCTGTGGTGGTTGCGCGTAACAACACGGACAAGCCGGTACGTA
TCGACGAAAGCCGATGCGGCGGTCGCTGGGTCATCGGCGTTGCGGCCTGGCCTCATGCATGGCTGCAGCCGGGTGAA
GAAAGTGAGGTGTACATCGCTGTGCGCCAGCCGCAGATATCTAAAATGGCCAAAGAAAGCAGGCCGTCACTGCTCCG
GGGAGCGAAACCATGA

Figure 10B

C.Disrupted *hrcC* gene; contains $Km^R$ cassette at *SphI* site

ATGTCGCTCGACATGTCGCCTGTCCAGGGCAAGCTCGATGGCCGTATTCGTGCTCAGAACCCTGAAGAGTTTCTTGA
GCGGCTGAGTCAGGAATACCACTTCCAGTGGTTCGTCTATAACGACACGCTGTATGTCAGCCCTTCCAGCGAGCACA
CCTCGGCGCGCATCGAAGTCTCGCCGGATGCGGTGGACGACCTGCAAACGGCGCTGACCGATGTCGGTCTGCTGGAC
AAGCGTTTTGGCTGGGGCTCGCTGCCTGACGAAGGCGTGGTTCTGGTTCGTGGTCCGGCCAAATACGTGGAGTTTGT
GCGCGACTACAGCAAGAAAGTCGAAAAGCCCGACGAGAAGGCCGACAAGCAAGATGTTGTCGTGCTGCCACTCAAAT
ACGCCAACGCGGCTGATCGGACTATTCGCTACCGTGACCAGCAGTTAGTGGTGGCCGGTGTCGCCAGTATTCTTCAA
GAGCTGCTGGAAAGCCGTTCGCGTGGCGAAAGCATTGACAGCGTGAACCTGTTGCCGGGGCAGGGCAGCAGTGTTGC
CAACAGCACAGGTGTCGCGGCCGCCGGCCTGCCTTACAACCTGGGCTCCAATGGTATCGATACGGGAGCACTGCAAC
AGGGCATTGACCGCGTATTGAACTTCAACAGCAAAAAAACTGCCAAGGGTCATGCCTCAGGCAAGGCAAATATCCGC
GTAAGCGCTGATGTGCGTAACAACTCCGTATTGATTTACGACCTGCCAGAGCGCAAGGCCATGTACCAGAAACTGGT
CAAGGAGCTGGACGTTCCGCGCAACCTGATCGAAATCGATGCGGTCATTCTCGACATCGACCGCAATGAACTGGCTG
AACTGTCCAGTCGCTGGAATTTCAATGCCGGCAGCGTCGGAGGTGGTGCCAACCTGTTTGATGCAGGCACCAGTTCA
ACGTTGTTCTTGCAGAACGCCAGCAAGTTTTCTGCCGAATTGCATGCCTGCAGTCGACTCTAGAGGATCCCGGGTAC
CGAGCTCGAATTCGCTAGCTTCACGCTGCCGCAAGCACTCAGGGCGCAAGGGCTGCTAAAGGAAGCGGAACACGTAG
AAAGCCAGTCCGCAGAAACGGTGCTGACCCCGGATGAATGTCAGCTACTGGGCTATCTGGACAAGGGAAAACGCAAG
CGCAAAGAGAAAGCAGGTAGCTTGCAGTGGGCTTACATGGCGATAGCTAGACTGGGCGGTTTTATGGACAGCAAGCG
AACCGGAATTGCCAGCTGGGGCGCCCTCTGGTAAGGTTGGGAAGCCCTGCAAAGTAAACTGGATGGCTTTCTTGCCG
CCAAGGATCTGATGGCGCAGGGGATCAAGATCTGATCAAGAGACAGGATGAGGATCGTTTCGCATGATTGAACAAGA
TGGATTGCACGCAGGTTCTCCGGCCGCTTGGGTGGAGAGGCTATTCGGCTATGACTGGGCACAACAGACAATCGGCT
GCTCTGATGCCGCCGTGTTCCGGCTGTCAGCGCAGGGGCGCCCGGTTCTTTTTGTCAAGACCGACCTGTCCGGTGCC
CTGAATGAACTCCAAGACGAGGCAGCGCGGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCGGGGCAGGATCTCCTGTCATCTCACCTTG
CTCCTGCCGAGAAAGTATCCATCATGGCTGATGCAATGCGGCGGCTGCATACGCTTGATCCGGCTACCTGCCCATTC
GACCACCAAGCGAAACATCGCATCGAGCGAGCACGTACTCGGATGGAAGCCGGTCTTGTCGATCAGGATGATCTGGA
CGAAGAGCATCAGGGGCTCGCGCCAGCCGAACTGTTCGCCAGGCTCAAGGCGCGGATGCCCGACGGCGAGGATCTCG
TCGTGACCCATGGCGATGCCTGCTTGCCGAATATCATGGTGGAAAATGGCCGCTTTTCTGGATTCATCGACTGTGGC
CGGCTGGGTGTGGCGGACCGCTATCAGGACATAGCGTTGGCTACCCGTGATATTGCTGAAGAGCTTGGCGGCGAATG
GGCTGACCGCTTCCTCGTGCTTTACGGTATCGCCGCTCCCGATTCGCAGCGCATCGCCTTCTATCGCCTTCTTGACG
AGTTCTTCTGAGCGGGACTCTGGGGTTCGAATTCGAGCTCGGTACCCGGGGATCCGTCGACTGCAGCATGCGCTTGA
AGGCAATGGTTCTGCGTCAGTCATCGGCAACCCGTCGATCCTGACCCTGGAGAATCAGCCTGCAGTGATCGACCTCA
GTCGCACCGAATACCTGACGGCCACTTCCGAGCGGGCCGCTGACATTCTGCCCATCACGGCGGGCACCAGCCTTCAA
GTGATTCCGCGTTCGCTGGACAACGATGGCAAGCCTCAGGTGCAAATGATCGTGGACATCGAGGATGGCCAGATCGA
TGTGTCGACGATCAATGACACCCAACCCAGTGTGCGCCGAGGCAATGTCAGCACCCAGGCGGTGATTGCCGAGCACG
GCTCGCTGGTCATCGGCGGCTTCCACGGTCTGGAAGCCAATGACAGGATTCACAAGATCCCGCTGTTGGGCGACATT
CCCTATATCGGCAAGCTGCTGTTCCAGTCCCGCAGTCGCGAACTGAGTCAGCGCGAGCGGCTGTTCATTCTGACCCC
TCGACTGATCGGCGATCAGGTCAATCCAGCACGCTATGTACAGAACGGCAACCCCCATGACGTCGATGACCAGATGA
AGAAAATCAAGGAACGACGTGACGGAGGCGAGCTGCCAACGCGGGGCGACATCCAGAAAGTCTTTACCCAAATGATC
GACGGCGCCGCCCCGGAAGGCCTGCGCGCTGGCCAGACCCTGCCCTTTGAAACCGATAGTCTGTGTGATCCGGGCGA
AGGTCTGACGCTTGATGGGCAGCGCTCGCAGTGGTTCGTCAAAAAAGACTGGGGTGTTGCTGTGGTGGTTGCGCGTA
ACAACACGGACAAGCCGGTACGTATCGACGAAAGCCGATGCGGCGGTCGCTGGGTCATCGGCGTTGCGGCCTGGCCT
CATGCATGGCTGCAGCCGGGTGAAGAAAGTGAGGTGTACATCGCTG

Figure 10C

OPTIMIZATION OF CORONATINE PRODUCTION IN A GENETICALLY IMPROVED STRAIN OF *PSEUDOMONAS SYRINGAE*

CROSS REFERENCE TO RELATED APPLICATIONS

This application claims the benefit of U.S. Provisional Patent Application Ser. No. 60/795,474, filed Apr. 27, 2006, and U.S. Provisional Patent Application Ser. No. 60/795,475, filed Apr. 27, 2006, the complete contents of both of which are hereby incorporated by reference.

SEQUENCE LISTING

This application includes as the Sequence Listing the complete contents of the accompanying text file "Sequence.txt", created Apr. 18, 2007, containing 8,336 bytes, hereby incorporated by reference.

BACKGROUND OF THE INVENTION

1. Technical Field

The present invention generally relates to stable bacterial strains that are genetically engineered to overproduce coronatine, as well as methods for optimizing the yield of coronatine from such strains. In particular, the invention provides APV1, a stable, genetically engineered strain of *Pseudomonas syringae* that overproduces coronatine at temperatures that are amenable to commercial production.

2. Background

Polyketides constitute a huge family of structurally diverse natural products including those with antibiotic, chemotherapeutic, and antiparasitic activities. Most of the research on polyketide synthesis in bacteria has focused on compounds synthesized by gram-positive bacterial species including *Streptomyces* and other actinomycetes (Hopwood, 1997; Katz, 1997). However, *Pseudomonas*, a gram-negative bacterium, produces a variety of antimicrobial compounds from the polyketide pathway including coronatine, mupirocin (pseudomonic acid), pyoluteorin, and 2,4-diacetylphloroglucinol (Bender et al., 1999).

With respect to coronatine (COR), the molecule is composed of two building blocks of distinct biosynthetic origin (Parry et al., 1994). One of these is the ethylcyclopropyl amino acid coronamic acid (CMA), which is derived from L-isoleucine via the intermediacy of L-alloisoleucine (Parry et al., 1994). The other component is coronafacic acid (CFA), which is a polyketide derived from acetate, butyrate, and a four-carbon unit derived from α-ketoglutarate (Parry et al., 1994; Parry et al., 1996). A brief overview of the biosynthetic route to coronatine is shown in FIG. 1. With reference thereto, COR consists of the polyketide component CFA coupled via amide bond formation to the amino acid component, CMA. CFA is a polyketide derived from three units of acetate, and one unit each of pyruvate and butyrate. CMA is derived from isoleucine via alloisoleucine. CFA can also be coupled to L-alloisoleucine (aile) and L-isoleucine (ile) to form the coronafacoyl analogues, CFA-aile and CFA-ile, respectively.

In plants infected with coronatine-producing bacteria, the primary symptom elicited by the presence of coronatine is a diffuse chlorosis that can be induced on a wide variety of plant species (Bender et al., 1999). Coronatine is also known to induce hypertrophy (cell enlargement), inhibit root elongation, and stimulate ethylene production in plants (Kenyon et al., 1992; Sakai et al., 1979). Several research groups have noted the remarkable structural and functional homologies between coronatine and methyl jasmonate (MeJA), a plant growth regulator derived from the octadecanoid signaling pathway, which is elicited by biological stress (Feys et al., 1994; Weiler et al., 1994). Coronatine and MeJA induce analogous biological responses in many plant tissues, and several researchers have suggested that coronatine functions as a molecular mimic of the octadecanoid signaling molecules produced by higher plants (Feys et al., 1994; Weiler et al., 1994). However, coronatine does not function solely as a molecular mimic of MeJA in some plant species (Palmer and Bender, 1995), and the mechanism of action for coronatine remains unclear.

While coronatine may cause undesirable effects in plants, it has also been shown to have great practical value, both as an abscission agent (see, e.g., U.S. patent Publication No. 20030013609 to Burns & Bender), and as a compound to increase taxane production (see U.S. patent Publication No. 20030175913 to Steele et al.), both of which are herein incorporated by reference.

Overproduction of coronatine by strain *Pseudomonas syringae* DC3000-hrcC has been described (Penaloza-Vazquez et al., 2000). DC3000-hrcC is a strain that contains a transposon insertion in the hrcC gene, which encodes a component of the type III secretion system. While strain DC3000-hrcC does overproduce coronatine, due to the unstable nature of the transposon insertion, this strain has been deemed unsuitable for commercial production of COR.

The prior art has thus far failed to provide stable bacterial strains capable of producing large quantities of coronatine under conditions that are suitable for commercial production.

SUMMARY OF THE INVENTION

The present invention provides novel, stable bacterial strains that are genetically engineered to overproduce coronatine. The bacterial strains are capable of producing coronatine under conditions that make their use in large scale commercial preparations of this compound feasible. Unlike overproducing strains that are unstable due to a transposon insertion, the strains provided herein are stable, genetically engineered strains that maintain the overproducing phenotype over time. One such exemplary strain is *Pseudomonas syringae* APV1 (ATCC deposit submitted 19 Apr. 2007, Patent Deposit Designation No. PTA-8340) which was produced by genetically engineering parent strain *P. syringae* DC3000 by stable insertion of the kanamycin resistance ($Km^r$) gene into the hrcC gene of the type III secretion system. In addition to stably producing higher yields of coronatine, the genetically engineered strains of the present invention do so at temperatures that are more amenable to bacterial cell culture than previously known overproducing strains (e.g. approximately 26° C. instead of 18° C.). Significantly, the strains are also non-pathogenic. In addition, the present invention provides cell culture methods for optimizing the yield of coronatine from the stable, overproducing strains.

The invention provides a stable genetically engineered bacterial strain that overproduces coronatine. In one embodiment, the stable bacterial strain is a *Pseudomonas syringae* bacterial strain. In another embodiment, the stable genetically engineered bacterial strain contains a genetically engineered mutation of a type III secretion system gene. In some embodiments, the genetically engineered mutation is an insertion of a stable genetic element, examples of which include but are not limited to antibiotic resistance cassettes such as the kanamycin resistance ($Km^r$) cassette. In one embodiment of the invention, the type III secretion system gene is hrcC. In yet another embodiment of the invention, the stable genetically engineered bacterial strain is non-pathogenic. The invention also provides a stable genetically engineered bacterial strain that overproduces coronatine, wherein the stable genetically engineered bacterial strain is a *Pseudomonas syringae* bacterial strain, and wherein the stable genetically engineered bacterial strain contains a genetically engineered mutation of a type III secretion system gene.

The invention further provides a method of producing coronatine. The method includes the steps of 1) culturing a stable genetically engineered bacterial strain that overproduces coronatine in a culture medium; and 2) removing coronatine produced by said stable genetically engineered bacterial strain in said culture medium. In one embodiment, the stable genetically engineered bacterial strain is immobilized on a matrix in the culture medium. In one embodiment, the stable genetically engineered bacterial strain is a *Pseudomonas syringae* bacterial strain. In yet another embodiment, the stable genetically engineered bacterial strain contains a genetically engineered mutation of a type III secretion system gene. The genetically engineered mutation may be, for example, the insertion of a stable genetic element, of which an antibiotic resistance cassette (e.g. a kanamycin resistance ($Km^r$) cassette) is one example. In one embodiment, the type III secretion system gene is hrcC. In one embodiment, the stable genetically engineered bacterial strain is non-pathogenic. In one embodiment of the invention, the step of culturing is carried out at approximately 26° C.

The invention further provides a method of inducing abscission in a plant. The method includes the step of applying to the plant coronatine that has been obtained from the stable genetically engineered bacterial strain that overproduces coronatine and that is non-pathogenic.

The invention further provides a method of inducing increased taxane production in plant cells. The method includes the step of applying to the plant cells coronatine that has been obtained from the stable genetically engineered bacterial strain that overproduces coronatine and that is non-pathogenic. The plant cells may be in a plant, or in a plant cell culture.

A better understanding of the present invention, its several aspects, and its advantages will become apparent to those skilled in the art from the following detailed description, taken in conjunction with the attached figures, wherein there is described the preferred embodiment of the invention, simply by way of illustration of the best mode contemplated for carrying out the invention.

BRIEF DESCRIPTION OF THE DRAWINGS

FIG. 10A-C. A, nucleotide sequence encoded by the $Km^r$ cassette (GenBank Accession No. M17626; SEQ ID NO: 1); B, nucleotide sequence of the hrcC gene (GenBank Accession No. AF232004; SEQ ID NO: 2); C, nucleotide sequence of the hrcC gene disrupted by the $Km^R$ cassette as it occurs in *P. syringae* strain APV1 (SEQ ID NO: 3). The boxed nucleotides indicate the SphI site; underlined nucleotides indicate the sequence of the $Km^R$ cassette.

DETAILED DESCRIPTION OF THE INVENTION

Before explaining the present invention in detail, it is important to understand that the invention is not limited in its application to the details of the embodiments and steps described herein. The invention is capable of other embodiments and of being practiced or carried out in a variety of ways. It is to be understood that the phraseology and terminology employed herein is for the purpose of description and not of limitation.

The present invention provides stable bacterial strains that are genetically engineered to overproduce coronatine, when compared to wild-type or parent strains of bacteria that have not been genetically engineered as described herein. Further, the bacterial strains do so under conditions that make their use in large scale preparation of coronatine feasible. In one embodiment of the invention, this is accomplished by genetically engineering a coronatine producing bacterial strain by inserting a stable genetic element into the hrcC gene, which encodes a component of the type III secretion system. This approach builds on existing knowledge of COR overproduction by strain *Pseudomonas syringae* DC3000-hrcC, a strain that contains a transposon insertion in hrcC (Peñaloza-Vázquez et al., 2000). Unfortunately, due to the unstable nature of the transposon insertion in DC3000-hrcC, this strain has been deemed unsuitable for commercial production of COR. Thus, one aim of the invention described below was to create new, stable coronatine-producing strains by inserting a stable genetic cassette into the hrcC gene. Because the cassettes that are utilized do not contain genes for transposition, they are genetically stable, and the genetically improved strains of the invention are therefore stable as well. In one exemplary embodiment, the stable cassette encodes kanamycin resistance ($Km^r$). Kanamycin is relatively inexpensive and has been used as a selectable marker in the construction of transgenic plants; consequently, use of this marker is an acceptable, economical method for selection of hrcC-mutated strains. Significantly, the COR-overproducing bacterial strains of the invention are also non-pathogenic.

One such exemplary strain is *Pseudomonas syringae* APV1, which was produced by genetically engineering parent strain *P. syringae* DC3000 by insertion of the kanamycin resistance ($Km^r$) gene into the hrcC gene. Without being bound by theory, the disruption of hrcC leads to an interruption in the transcription of hrcC, hrpT, and hrpV(Peñaloza-Vázquez et al., 2000; also see FIG. 3). It is important to note that hrpV is a regulatory gene, and it is believed that the mutation of hrpV leads to an overproduction of coronatine.

Figure 4:
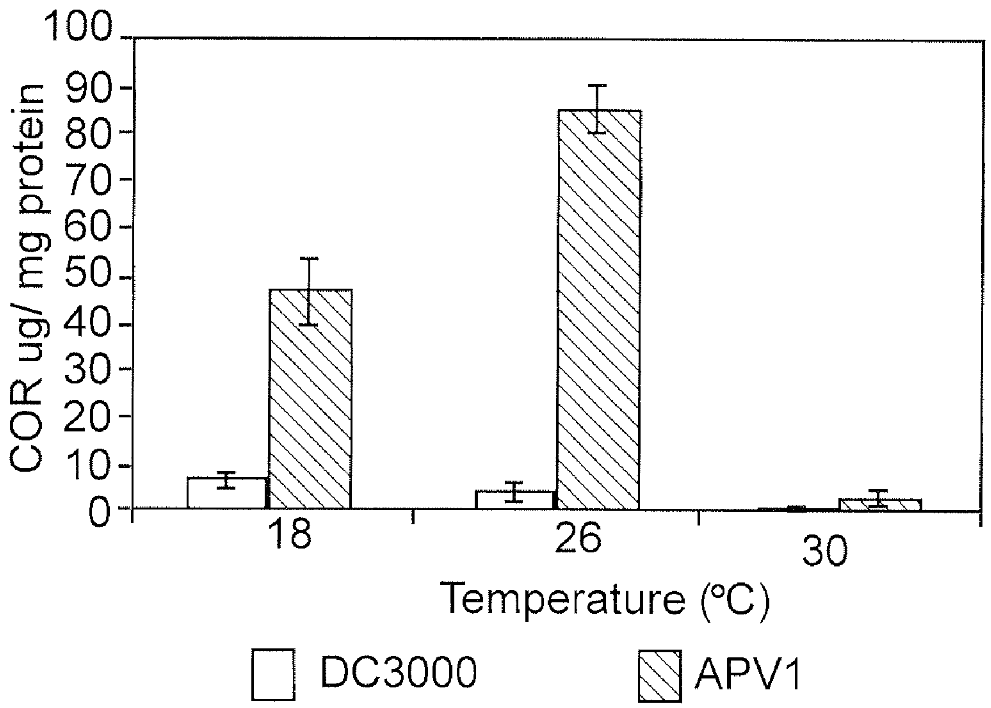
FIG. 4. Production of COR by *P. syringae* DC3000 and APV1 (genetically modified derivative of DC3000) at 18, 26 and 30° C. Values represent the means from one experiment containing three replicates per strain, and vertical bars indicate the SEM. The experiment was repeated with similar results.

In addition to producing higher yields of coronatine, the genetically engineered strains of the present invention do so at temperatures that are more amenable to bacterial cell culture than previously known overproducing strains (e.g. 26° C. instead of 18° C.; see FIG. 4). The stable overproducing strains of the invention are thus suitable for use in the large scale commercial preparation of coronatine. In addition, the present invention provides methods for optimizing the yield of coronatine from overproducing strains, e.g. by immobilization of the stable, overproducing bacteria during culture.

Figure 2:
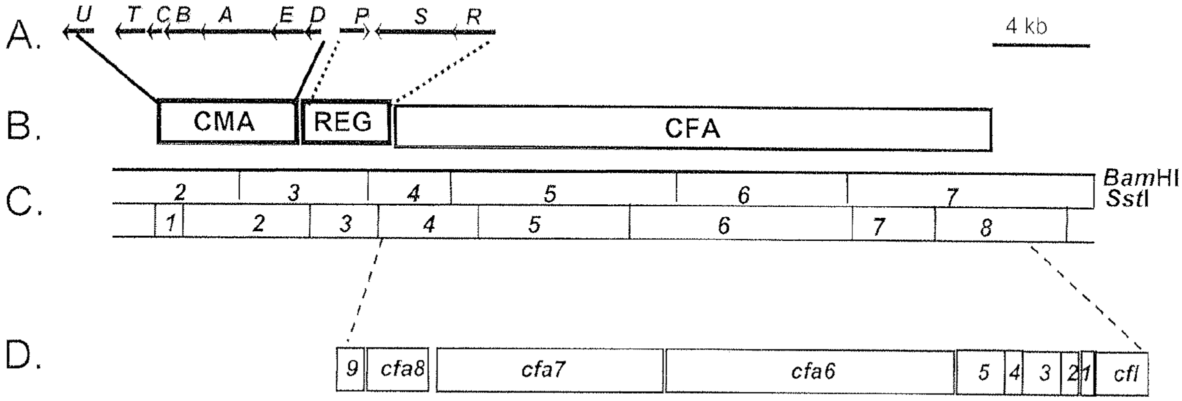
FIG. 2 is a functional and physical map of the coronatine biosynthetic gene cluster in *Pseudomonas syringae* pv. *glycinea* PG4180.

Coronatine biosynthesis has been intensively studied in *Pseudomonas syringae* pv. *glycinea* PG4180 because this strain is easy to manipulate genetically, consistently synthesizes large amounts of coronatine in vitro (20-40 mg/L), and infects soybean, a host which is easy to cultivate. The coronatine biosynthesis genes in *P. syringae* pv. *glycinea* PG4180 are encoded by a 90-kb plasmid designated p4180A (Bender et al., 1993). A 32.8-kb contiguous region of plasmid p4180A is required for coronatine biosynthesis, and a physical map of the coronatine gene cluster was developed using the restriction enzymes BamHI and SstI (see FIG. 2C). Two regions in the coronatine biosynthetic cluster contain structural genes for coronamic and coronafacic acid biosynthesis; these regions are separated by a 3.4-kb regulatory region (REG, FIG. 2B). The nucleotide sequence of the 6.9-kb region containing the coronamic acid biosynthetic gene cluster revealed the presence of seven genes designated cmaD, cmaE, cmaA, cmaB, cmaC, cmaT, and cmaU, the sequences of which are known and accessible under GenBank accession number AY391839 (all subsequent references to accession numbers refer to GenBank accession numbers, unless otherwise indicated) (Budde et al., 1998; Couch et al., 2004; Ullrich and Bender, 1994). The deduced amino acid sequence encoded by cmaD shows relatedness to acyl carrier proteins and contains a phosphopantheteine attachment site, whereas the amino acid sequence encoded by cmaE shows similarity to proteins with alpha/beta hydrolase folds. The protein product of cmaA was shown to activate and load alloisoleucine for use in coronamic acid biosynthesis (Couch et al., 2004). CmaB chlorinates the γ position of the L-allo-isoleucine, and CmaC catalyzes the formation of the cyclopropyl ring from the chlorinated L-allo-isoleucine; the latter is then covalently attached to CmaD by CmaA and CmaE (Vaillancourt et al., 2005). CmaT was shown to have thioester activity (Patel et al., 1998) and may be involved in the release of free CMA (Couch et al., 2004). The last gene in the CMA region is cmaU, the protein product of which is related to amino acid efflux proteins and may be required for the export of either CMA or coronatine from the cell.

Coronafacic acid biosynthesis requires cfa1, cfa2, and cfa3 (deposited as #U56980), which encode monofunctional proteins similar to the acyl carrier protein, dehydratase, and β-ketoacyl synthase, respectively, of type II polyketide synthases. Other genes required for coronafacic biosynthesis include cfa4 (#JC5748), cfl (#U09027), and cfa5 (#PC4426); the latter two genes exhibit an acyl adenylate/CoA ligase signature (Liyanage et al., 1995; Penfold et al., 1996). Two adjacent genes (cfa6, cfa7) (#AF098795) in the coronafacic acid biosynthetic gene cluster encode modular type I polyketide synthase (PKS) proteins that are required for coronafacic acid biosynthesis (Rangaswamy et al., 1998). Two additional genes in the coronafacic acid biosynthetic cluster, cfa8 and cfa9 (#AF061506), show relatedness to crotonyl-CoA reductases and thioesterases, respectively. Therefore, the complete coronafacic acid PKS exhibits a combination of multifunctional and monofunctional polyketide synthase proteins.

A regulatory region was isolated which controls both coronafacic and coronamic acid production; the nucleotide sequence of this region revealed the presence of three genes, corP (#U33327), corS (#U33326), and corR (#U33326) (FIG. 2A) (Ullrich et al., 1995). The deduced amino acid sequences of corP and corR indicated relatedness to response regulators that function as members of two-component regulatory systems, and the translational product of corS showed sequence similarity to histidine protein kinases that function as environmental sensors (Ullrich et al., 1995). CorS functions as a histidine protein kinase and phosphorylates CorR (Rangaswamy and Bender, 2000). CorR functions as a positive activator of coronatine gene expression by binding to the promoter regions of the coronafacic and coronamic acid transcripts (Peñaloza-Vázquez and Bender, 1998; Wang et al., 1999).

The invention is based in part on the development of genetically engineered stable bacterial strains that overproduce coronatine. By "overproduce" we mean that the genetically engineered bacteria produce a higher level (i.e. a greater amount or quantity) of coronatine than the parent strain from which they are derived or constructed, when cultured under the same conditions. The parent strain may be a wild type bacterial strain, or a bacterial strain that has already undergone strain selection, genetic manipulation, or other procedures in the laboratory. For purposes of the present invention, the parent strain is considered to be the bacterial strain that undergoes genetic manipulation to produce the genetically engineered, stable overproducing strain of the invention, and the overproducing stains of the invention are "from" or "of" these parental stains. In general, the novel overproducing strains of the invention will produce at least about 5 fold or more coronatine than does the parental strain, or preferably at least about 10 fold or more coronatine, or more preferably at least about 15 to 20 fold, or even more (e.g. about 25-50, or even 100 fold more) coronatine.

By "stable" we mean that the genetic manipulation that is undertaken to produce the overproducing strains of the present application results in a permanent alteration to the bacterial genome that is stably transmissible to progeny of the genetically engineered bacteria. Further, the phenotypic expression of the genetic alteration is also displayed by the progeny of the genetically engineered bacteria, i.e. the progeny also overproduce coronatine. Those of skill in the art will recognize that, as with all living organisms, bacteria are susceptible to occasional random genetic mutations due to a variety of factors, and if any such mutations (e.g. point mutations, insertions, deletions, etc.) occur in the overproducing strains of the present invention, the bacterial strains so mutated are still to be considered within the purview of the present invention, so long as the bacteria still overproduce coronatine. Likewise, further purposeful genetic alterations may be introduced into the overproducing strains of the invention for other purposes, (e.g. insertion of a superpromoter, insertion of genes encoding a labeling entity or characteristic such as fluorescence, insertion of antibiotic resistance genes, etc.). However, all such further genetic alterations of the overproducing strains of the invention are also contemplated in the present invention, so long as the resulting bacterial strain retains the ability to stably overproduce coronatine.

By "bacterial strain" we mean the bacterium or bacteria that was originally genetically engineered, and all progeny thereof.

In a preferred embodiment of the invention, the parental and genetically engineered overproducing bacterial strains are of *Pseudomonas syringae* origin. *Pseudomonas syringae* is the only bacterium currently known to produce coronatine. However, other bacteria are known to produce coronatine analogs (e.g. *Xanthomonas campestris pv phormiicola*; and some other bacteria are known to have some of the coronatine genes (e.g. *Erwinia carotovora*). These and any other strains that, for example, could be genetically engineered to contain the genes for synthesis of coronatine, may also be used in the practice of the present invention.

In a preferred embodiment of the invention, overproduction of coronatine results from the inactivation of a gene of the type III secretion pathway. By "inactivation" we mean that as a result of the genetic engineering, the gene product can no longer fulfill its usual function in the pathway. The gene product may not be transcribed, or be transcribed but not be translated, or a defective gene product that is not capable of carrying out the usual function of the normal gene product may be produced instead. Alternatively, the amount of effective gene product that is produced may be very low, so much so that the pathway as a whole does not function properly. In one embodiment of the invention, this is realized by insertion of a genetic element into the hrcC gene of the type III secretion pathway. Without being bound by theory, such an insertion appears to block accurate transcription and/or translation of the gene product of this gene and downstream genes hrpT and hrpV, thus disarming the type III secretion pathway. However, those of skill in the art will recognize that transcription and/or translation of other genes in other pathways may also be carried out to generate overproducing COR bacteria. Examples include but are not limited to, for example, gacA and gacS. Further, other genes of the type III secretion pathway may be targeted for mutation/interruption of transcription or translation (or translation of a non-functioning gene product), e.g. (hrpT, hrpV and/or hrpS). In addition, one or more of such genetically engineered mutations may be carried out to produce the COR-overproducing bacteria of the invention, so long as the resulting bacteria are viable, overproduce COR, and the genetic change is stable. However, in a preferred embodiment, the gene is hrcC. This is due, in part to, for example, the small (and therefore inconvenient) size of e.g. hrpV, and the advantage of rendering the bacterium non-pathogenic by mutation of hrcC, which encodes a structural portion of the type III secretion system.

Further, other means of preventing the transcription and/or translation of the hrcC (or another) gene may also be used and would result in increased production of coronatine, e.g. deletion and or replacement of all or portions of the gene, insertion of a stop codon into the gene, introduction of mutations into the gene, gene silencing, etc. All such means are intended to be encompassed by the present invention. In addition, other means of preventing transcription and/or translation or the gene or proper functioning or usual activity of the gene product may also occur to those of skill in the art (e.g. the use of inhibitory RNA), and are within the scope of the present invention.

In one embodiment of the invention, a $Km^r$ cassette is inserted into a gene (e.g. hrcC gene) in order to produce the bacterial strains of the invention. However, those of skill in the art will recognize that other stable genetic elements or cassettes may also be used in a similar manner and with similar results. For example, cassettes encoding other antibiotic resistance genes may be utilized (e.g. resistance to chloramphenicol, streptomycin, spectinomycin, tetracycline, gentamicin, etc.,) as well as cassettes encoding reporter genes (e.g. glucuronidase, luciferase, green fluorescent protein, and the like).

In some embodiments, the genetically engineered strains of the present invention produce coronatine at temperatures that are more amenable to bacterial cell culture than previously known overproducing strains. In one embodiment of the invention, the overproducing strains produce COR at temperatures that are greater than about 20° C., and preferably at temperatures that are greater than about 25° C. (e.g. about 26° C. or higher). In one embodiment, COR is produced at temperatures ranging from about 20° C. to about 30° C. This confers a distinct advantage since this temperature range is much easier to maintain in a bacterial cell culture setting (e.g. for larger scale fermentations) than is the previously required temperature (18° C.). For the purposes of the present invention, the temperature of cultivation of the overproducing strains may be the optimal temperature for COR production. However, this is not an absolute requirement. The temperature at which the overproducing bacteria are cultivated need not be the absolute optimum, but rather a temperature at which sufficient COR can be produced to outweigh the practical constraints of maintaining a lower or higher temperature, i.e. the actual optimal yield may be sacrificed in order to maintain an environment that is readily achieved and maintained.

Figure 1:
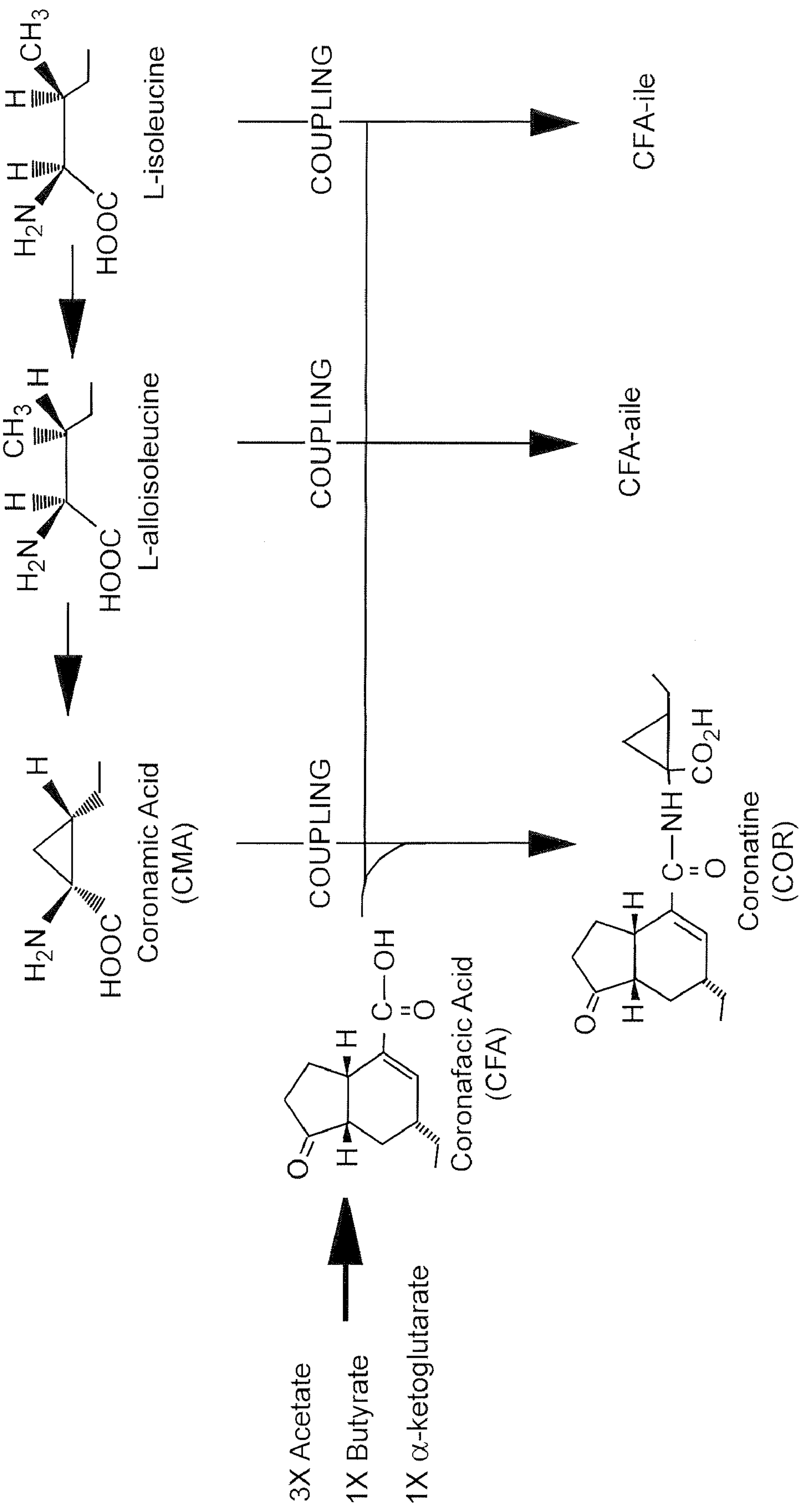
FIG. 1 is a schematic diagram illustrating the biochemical pathways involved in the synthesis of coronatine and coronafacoyl compounds.

In a preferred embodiment of the invention, the COR overproducing bacterial strain is APV1, which is derived from *P. syringae* DC3000. In APV1, a kanamycin resistance ($Km^r$) cassette has been inserted into the hrcC gene of the gene cluster that encodes the type III secretion system. The amino acid sequence of the $Km^R$ cassette is provided in FIG. 10A. The nucleotide sequence of the hrcC gene is provided in FIG. 10B (see GenBank Accession No. AF232004). The $Km^R$ cassette was inserted into the SphI site in hrcC (see FIG. 1C). Those of skill in the art will recognize that many nucleotide sequences can encode such an amino acid sequence (e.g. due to the redundancy of the DNA encoding mechanism) and all such possible nucleotide sequences (DNA, RNA, etc.) are contemplated for use in the present invention. Further, many plasmids or other constructs useful for genetic engineering may be utilized to make the bacterial strains of the invention. An exemplary sequence is that within the operon presented in GenBank Accession No. AF232004. In APV1, the cassette was inserted in the middle of the gene at the SphI restriction site; however, those of skill in the art will recognize that the insertion may be at any location within the gene, and in either orientation, so long as the insertion disrupts the normal functioning of or disables the gene product, and preferably, of downstream gene products as well.

The COR-overproducing bacterial strains of the present invention are non-pathogenic. As such, they may safely be used for direct application to plants for any of a variety of reasons, including but not limited to: to induce abscission or fruit loosening to facilitate mechanical harvesting of fruit, thereby bypassing the expense of hiring labor for manual harvesting by hand; and to induce higher taxane production by or in plants to which they are applied. In the latter example, it is important to mention that coronatine stimulates the production of diterpene taxanes in cell cultures of *Taxus* spp. And this has resulted in a patent application for the use of COR and related compounds as elicitors of taxol production (see U.S. patent Publication No. 20030175913 to Steele et al., which is herein incorporated by reference). The present invention thus also provides methods for inducing abscission in plants and methods for inducing increased taxane production in plants, by application to the plant of a non-pathogenic COR-overproducing bacterial strain of the invention. Alternatively, COR overproduced by the methods of the invention may be applied directly to plants to achieve similar results.

The present invention also provides methods of making or producing coronatine using the overproducing strains of the invention. In general, the bacterial strains are cultivated with a suitable media (e.g. HSS, HSC, and the like) according to methods that are well established in the art (e.g. under sterile conditions, with suitable aeration, etc). The coronatine is then removed from the culture media by known methods, e.g. organic extraction with ethyl acetate, and may then be further purified, concentrated, etc.

It has been discovered that immobilization of the COR-overproducing bacterial cells of the invention on a matrix results in further higher yields of COR. Therefore, in a preferred embodiment of the invention, the overproducing bacteria are immobilized on a matrix. Immobilization appears to protect the cells and to protect cell viability. Those of skill in the art will recognize that several techniques and matrices for immobilizing bacterial cell cultures are available, and all such techniques and matrices are intended to be encompassed by the present invention. However, in preferred embodiments, the immobilization matrix is calcium alginate or Cytoline™ 2. Examples of other suitable matrices include but are not limited to porous glass beads and solid PVA particles, wood chips, diatomaceous earth beads, carrageenan, chitosan and polysaccharide gels.

REFERENCES FOR BACKGROUND OF THE INVENTION

Bender, C. L., F. Alarcón-Chaidez, and D. C. Gross. 1999. *Pseudomonas syringae* phytotoxins: mode of action, regulation and biosynthesis by peptide and polyketide synthetases. Microbiol. Mol. Biol. Rev. 63:266-292.

Bender, C. L., H. Liyanage, D. Palmer, M. Ullrich, S. Young, and R. Mitchell. 1993. Characterization of the genes controlling biosynthesis of the polyketide phytotoxin coronatine including conjugation between coronafacic and coronamic acid. Gene 133:31-38.

Bucke, C. 1987. Cell immobilization in calcium alginate. In Immobilization Techniques for cells/organelles. Meth. Enzymol. 135:175-189.

Budde, I. P., B. H. Rohde, C. L. Bender, and M. S. Ullrich. 1998. Growth phase and temperature influence promoter activity, transcript abundance and protein stability during biosynthesis of the *Pseudomonas syringae* phytotoxin coronatine. J. Bacteriol. 180:1360-1367;

Burns, J. K., Pozo, L. V., Arias, C. R., Hockema, B., Rangaswamy, V., and Bender, C. L. 2003. Coronatine and abscission in citrus. J. Amer. Soc. Hort. Sci. 128: 309-315.

Couch, R.; O'Connor, S. E.; Seidle, H.; Walsh, C. T., and Parry, R. Characterization of CmaA, an adenylation-thiolation didomain enzyme involved in the biosynthesis of coronatine. J. Bacteriol. 2004 January; 186(1):35-42.;

Feys, B., Penfold, C. and Turner, J. (1994) *Arabidopsis* mutants selected for resistance to the phytotoxin coronatine are male sterile, insensitive to methyl jasmonate, and resistant to a bacterial phytotoxin. Plant Cell 6: 751-759.

Hopwood, D. A. 1997. Genetic contributions to understanding polyketide synthases. Chem. Rev. 97:2465-2497.

Ichihara, A., Shiraishi, K., Sato, H., Sakamura, S., Nishiyama, K., Sakai, R., Furusaki, A., and Matsumoto, T. (1977) The structure of coronatine. J. Am. Chem. Soc. 99: 636-637.

Katz, L. 1997. Manipulation of modular polyketide synthetases. Chem. Rev. 97:2557-2575.

Kenyon, J. S., and J. G. Turner. 1992. The stimulation of ethylene synthesis in *Nicotiana tabacum* leaves by the phytotoxin coronatine. Plant Physiol. 100:219-224.

Liyanage, H., C. Penfold, J. Turner, and C. L. Bender. 1995. Sequence, expression and transcriptional analysis of the coronafacate ligase-encoding gene required for coronatine biosynthesis by *Pseudomonas syringae*. Gene 153:17-23.

Palmer, D. A., and Bender, C. L. (1995) Ultrastructure of tomato leaf tissue treated with the Pseudomonad phytotoxin coronatine and comparison with methyl jasmonate. Mol. Plant-Microbe Interact. 8: 683-692.

Parry, R. J., S. Jiralerspong, S. Mhaskar, L. Alemany, and R. Willcott. 1996. Investigations of coronatine biosynthesis. Elucidation of the mode of incorporation of pyruvate into coronafacic acid. J. Am. Chem. Soc. 118:703-704.

Parry, R. J., S. V. Mhaskar, M.-T. Lin, A. E. Walker, and R. Mafoti. 1994. Investigations of the biosynthesis of the phytotoxin coronatine. Can. J. Chem. 72:86-99.

Patel, J., J. C. Hoyt, and R. J. Parry. 1998. Investigations of coronatine biosynthesis. Overexpression and assay of CmaT, a thioesterase involved in coronamic acid biosynthesis. Tetrahedron 54:15927-1593.

Peñaloza-Vázquez, A., and C. L. Bender. 1998. Characterization of C or R, a transcriptional activator which is required for biosynthesis of the phytotoxin coronatine. J. Bacteriol. 180:6252-6259.

Penaloza-Vazquez, A., Preston, G. M., Collmer, A., and Bender, C. L. (2000) Regulatory interactions between the Hrp type III protein secretion system and coronatine biosynthesis in *Pseudomonas syringae* pv. tomato DC3000. Microbiology 146: 2447-2456.

Penfold, C. N., C. L. Bender, and J. G. Turner. 1996. Characterisation of genes involved in biosynthesis of coronafacic acid, the polyketide component of the phytotoxin coronatine. Gene 183:7-173.

Rangaswamy, V., and C. L. Bender. 2000. Phosphorylation of C or S and C or R, regulatory proteins that modulate production of the phytotoxin coronatine in *Pseudomonas syringae*. FEMS Microbiol. Lett. 193:13-18.

Rangaswamy, V., S. Jiralerspong, R. Parry and C. L. Bender. 1998. Biosynthesis of the *Pseudomonas* polyketide coronafacic acid requires monofunctional and multifunctional polyketide synthase proteins. Proc. Natl. Acad. Sci. USA 95:15469-15474.

Sakai, R., K. Nishiyama, A. Ichihara, K. Shiraishi, and S. Sakamura. 1979. The relation between bacterial toxic action and plant growth regulation, p. 165-179. In J. M. Daly and I. Uritani (ed.), Recognition and specificity in plant host-parasite interactions. University Park Press, Baltimore.

Ullrich, M., and C. L. Bender. 1994. The biosynthetic gene cluster for coronamic acid, an ethylcyclopropyl amino acid, contains genes homologous to amino acid-activating enzymes and thioesterases. J. Bacteriol. 176:7574-7586.
Ullrich, M., Penaloza-Vazquez, A., Bailey, A. M., and Bender, C. L. (1995) A modified two-component regulatory system is involved in temperature-dependent biosynthesis of the *Pseudomonas syringae* phytotoxin coronatine. J. Bacteriol. 177: 6160-6169.
Vaillancourt, F. H.; Yeh, E.; Vosburg, D. A.; O'Connor, S. E., and Walsh, C. T. Cryptic chlorination by a non-haem iron enzyme during cyclopropyl amino acid biosynthesis. Nature. 2005 Aug. 25; 436(7054):1191-1194.
Wang, L., C. L. Bender, and M. S. Ullrich. 1999. The transcriptional activator C or R is involved in biosynthesis of the phytotoxin coronatine and binds to the cmaABT promoter region in a temperature-dependent manner. Mol. Gen. Genet. 262:250-260
Weiler, E. W., T. M. Kutchan, T. Gorba, W. Brodschelm, U. Neisel, and F. Bublitz. 1994. The *Pseudomonas* phytotoxin coronatine mimics octadecanoid signaling molecules of higher plants. FEBS Lett. 345:9-13.

The present invention will be further understood with reference to the following non-limiting experimental examples.

EXAMPLES

Example 1

Genetically Improved Strains for Coronatine Production

Use of the phytohormone coronatine (COR) as an abscission aid in the mechanical harvesting of citrus fruit has been described (see U.S. Pat. No. 6,511,939 to Burns et al., entitled "Coronatine as an Abscission Agent for Citrus," the complete contents of which is incorporated herein by reference). However, a critical issue regarding the further development and utilization of COR is the low yield of the compound obtained by fermentation of COR-producing bacteria. Consequently, the aim of this invention was to improve the yields of COR through bacterial strain improvement. The approach used builds on existing knowledge of COR overproduction by strain *Pseudomonas syringae* DC3000-hrcC, a strain that contains a transposon insertion in hrcC, which encodes a component of the type III secretion system (Peñaloza-Vázquez et al., 2000). Due to the unstable nature of the transposon insertion in DC3000-hrcC, this strain was deemed unsuitable for commercial production of COR. Thus, the aim of the invention described below was to create a new, stable derivative of DC3000 by inserting a genetic cassette encoding kanamycin resistance ($Km^r$) into the hrcC gene. Kanamycin is relatively inexpensive and has been used as a selectable marker in the construction of transgenic plants; consequently, this marker was chosen because it is predicted to be an acceptable, economical method for selection of hrcC-mutated strains. The $Km^r$ cassette is genetically stable (it does not contain genes for transposition), and the genetically improved strain that has been identified has several key characteristics that make it attractive for production of COR.

Background Information

Structure of coronatine. COR is an unusual molecule that can be hydrolyzed to yield two distinct components: (i) the polyketide coronafacic acid (CFA), and (ii) coronamic acid (CMA), an ethylcyclopropyl amino acid derived from isoleucine (FIG. 1) (Ichihara et al., 1977). The structure and absolute stereochemistry of CFA were elucidated by X-ray crystallography, and the absolute stereochemistry of CMA was established by X-ray analysis of its N-acetyl derivative (Ichihara et al., 1977). Coronatine is generally the predominant coronafacoyl compound synthesized by *Pseudomonas syringae*. The coronafacic acid (CFA) portion of COR shares structural and functional similarities to jasmonic acid (Feys et al., 1994; Weiler et al., 1994) (FIG. 1), leading many researchers to assume that COR functions as a molecular mimic of jasmonate. However, the coronamic acid (CMA) portion of COR is a structural analogue of aminocyclopropyl carboxylic acid (ACC), the immediate precursor of ethylene (Ferguson and Mitchell, 1985). The CMA portion of COR imparts additional biological activities to COR that are not induced by CFA alone (Palmer and Bender, 1995). In summary, the unique biological activities associated with COR suggest that it functions as a phytohormone, and this prompted investigations of the use of COR as an abscission aid for mechanical harvesting (Burns et al., 2003). Since a synthetic source of COR is not available, COR is currently obtained from the fermentation of the producing bacterium, *Pseudomonas syringae*. However, yields of COR from bacterial fermentations are low and remain a limiting factor in the utilization of COR as an abscission aid. In this Example, the development of an improved bacterial strain (designated APV1) that produces significantly higher amounts of COR than the parent strain (DC3000) is described.

Figure 3:
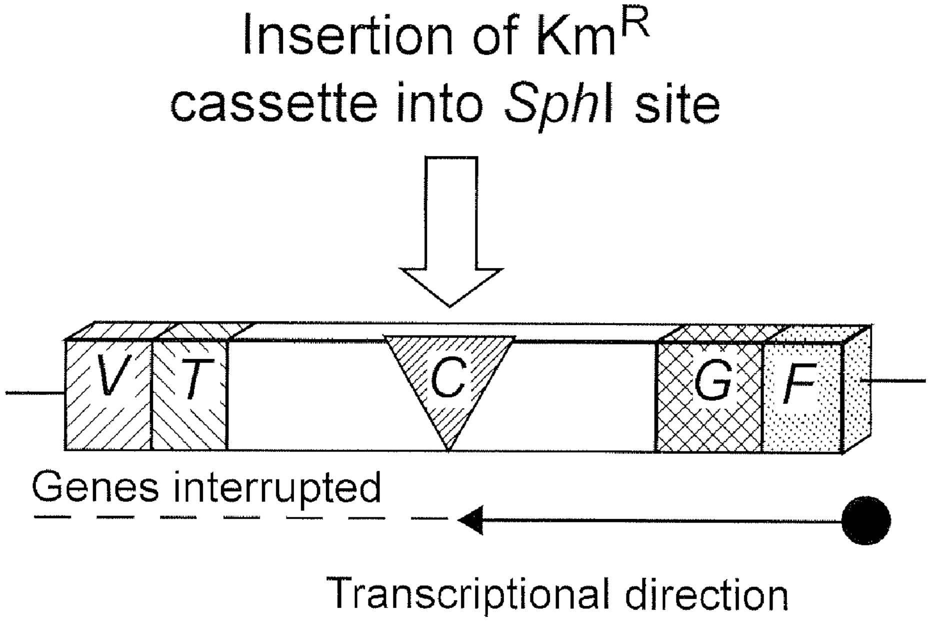
FIG. 3. Insertion of a $Km^R$ resistance cassette into the hrcC gene of *Pseudomonas syringae* DC3000. The insertion leads to a mutation in hrcC and the two downstream genes (hrpT and hrp V). The result is a nonpathogenic strain of *P. syringae* that overproduces coronatine.

Construction of the genetically modified strain, APV1. The goal of the experiments described herein was to generate a COR-overproducing strain of *P. syringae* by inserting a kanamycin resistance ($Km^r$) cassette into the hrcC gene of *P. syringae* DC3000 (FIG. 3). First, the hrcC gene was amplified from genomic DNA of *P. syringae* DC3000 using the polymerase chain reaction (PCR). The amplified hrcC gene was then cloned into the EcoRI restriction site present in pBluescript SK+. The resulting construct was digested with SphI, which cleaves hrcC once in the middle of the gene, but does not cut the vector, pBS. A $Km^r$ cassette (Alexeyev, 1995) was ligated into the hrcC gene at the SphI site, resulting in a cloned copy of hrcC::$Km^r$. The construct containing hrcC::$Km^r$ was introduced into DC3000 and recombined into the genome using homologous recombination (Bender, et al. 1991). *P. syringae* DC3000 recombinants containing a $Km^r$-disrupted copy of hrcC (replacement of hrcC with hrcC::$Km^r$) were selected on media containing kanamycin and analyzed by Southern blotting and PCR (Keith and Bender, 1999; Yu et al., 1999). The outcome was a COR-overproducing strain of *P. syringae* with a stable, selectable marker for maintaining the hrcC mutation (e.g. kanamycin), and this derivative strain was designated APV1.

*P. syringae* APV1 produces high levels of COR at 26° C. A variety of nutritional and environmental factors have been previously examined to determine their effect on COR production in the related strain, *P. syringae* pv. *glycinea* PG4180. Temperature had a highly significant effect on COR biosynthesis and cor gene expression in PG4180, and 18° C. was an optimal temperature for both COR production and cor gene transcriptional activity (Palmer and Bender, 1993; Ullrich et al., 1995; Rohde et al., 1998) showed that COR production was thermoregulated in many strains of *P. syringae* pvs. *atropurpurea, maculicola, morsprunorum*, and tomato, which may indicate that temperature is a common regulatory control for COR biosynthesis in other pathovars of *P. syringae*. The requirement of a low temperature for COR synthesis increases the cost of producing COR because the bacterial fermentation must be refrigerated. Thus we wanted to develop a strain of *P. syringae* that produced COR at conditions more favorable for large scale fermentation.

COR production by the parent strain DC3000 and the genetically improved strain, APV1, was examined at 18, 26 and 30° C. It was found that APV1 produced approximately 15 to 20-fold more COR than the parent strain, DC3000 (FIG. 4). Production of COR by the modified strain, APV1, was highest at 26° C., a temperature much more favorable for large-scale fermentation than 18° C. (the optimum for the parent strain, DC3000). In both strains, COR production was negligible when the fermentation was conducted at 30° C. In summary, APV1 produces optimal levels of COR at 26° C., a temperature more appropriate for large scale fermentations.

Figure 5:
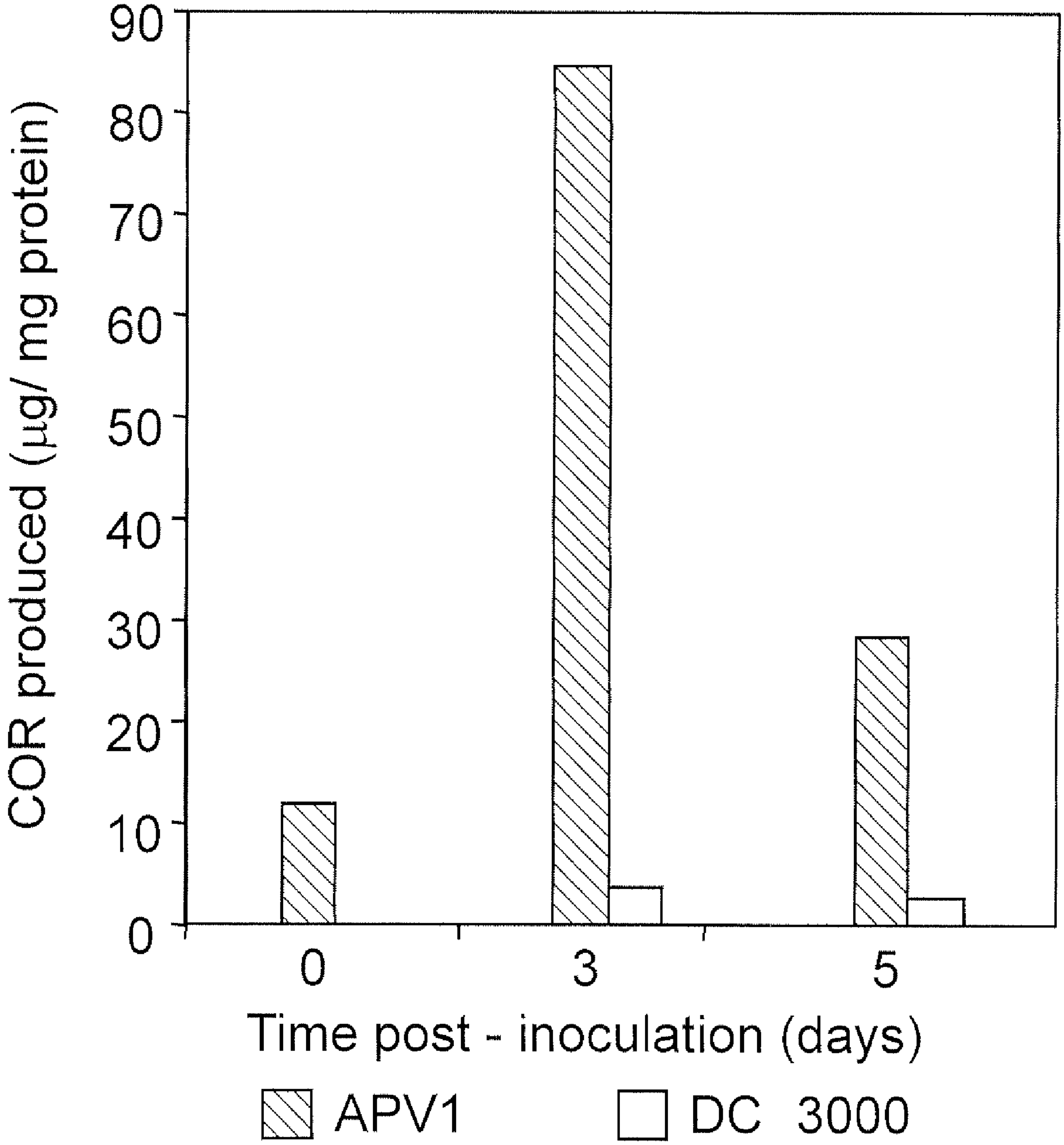
FIG. 5. Coronatine production by *Pseudomonas syringae* DC3000 (parent strain) and APV1 (improved strain). The initial inoculum was adjusted to an $OD_{600}$ nm of 0.1 in HSS medium (Peñaloza-Vázquez et al., 2000), and incubated with shaking (250 rpm.) at 26° C. Aliquots of the two strains (three replicates per sampling) were removed at 0, 3, and 5 days, and evaluated for COR production by HPLC.

Another constraint to producing COR on a large-scale basis is the length of the fermentation period for optimal COR production. In *P. syringae* pv. *glycinea* PG4180, optimal COR production required a 7-day incubation period (Palmer and Bender, 1993). Thus we examined whether this would be true for the genetically improved strain, APV1. The results shown below (FIG. 5) indicate that APV1 produces a large amount of COR when incubated for a 3-day period at 26° C. Therefore, the constraint of a long incubation period has been circumvented in strain APV1. Further optimization of COR yields are disclosed in Example 2 below.

The genes for pathogenicity are disabled in the genetically improved strain, APV1. In *P. syringae* pv. tomato DC3000, the type III secretion system (TTSS), which is encoded by the hrp/hrc gene cluster, is required for pathogenicity (Jin et al., 2003) and the ability to grow within or on the surface of plants (Hirano et al., 1999). Therefore, disruptions in the hrp genes render *P. syringae* nonpathogenic and unable to fully colonize the surfaces of plant parts. The use of a nonpathogenic strain of *P. syringae* for the production of COR in bacterial fermentations is desirable in terms of future use of the genetically improved strain for large-scale COR production. Thus, the genetically improved strain, APV1, was tested for its ability to colonize and cause disease on plants (Peñaloza-Vázquez et al., 2000). Strain APV1 contains a mutation in the hrcC gene, which should render the strain both nonpathogenic and impaired for its ability to colonize plants.

Figure 6C:
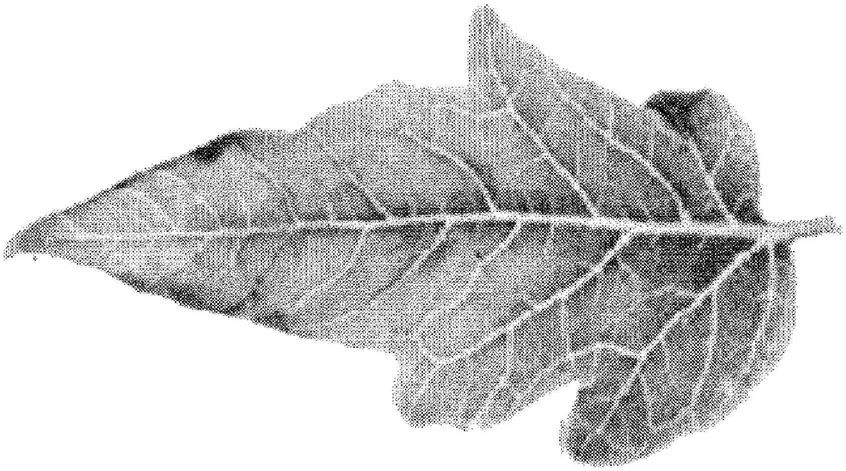
FIG. 6A-C. Tomato leaves sprayed with (a) *P. syringae* DC3000 (parent strain), (b) APV1 (strain improved for COR production) and (c) water. Photographs were taken 7 days after inoculation.
Figure 6B:
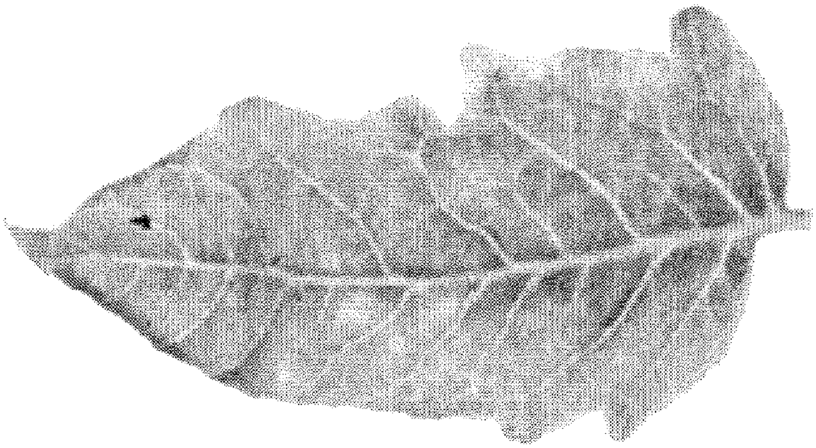
Figure 6A:
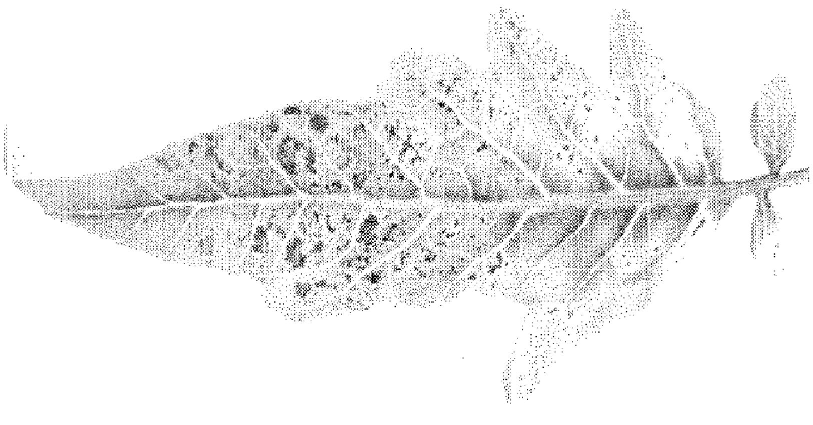

Tomato leaves were inoculated with *P. syringae* DC3000 (parent strain) and APV1 (the genetically improved strain that overproduces COR) by spraying tomato leaves with inoculum ($10^6$ cfu/ml) until leaf surfaces were uniformly wet. After inoculation, all plants were incubated in a growth chamber with a 12 h photoperiod at 24° C. and 90% relative humidity. Leaves sprayed with the parent strain DC3000 were severely diseased (FIG. 6*a*), whereas those inoculated with strain APV1 were virtually symptom free (FIG. 6*b*).

The ability of DC3000 (parent strain) and APV1 (our modified strain) to colonize leaves of tomato, the host of *P. syringae* pv. tomato DC3000, was also monitored. Tomato leaves were sprayed with *P. syringae* pv. tomato DC3000 and APV1 ($10^6$ cfu/ml) until surfaces were uniformly wet. After inoculation, all plants were incubated in a growth chamber with a 12 h photoperiod at 24° C. with 90% relative humidity. Leaves were sampled for the bacterial population using well-established methods (Peñaloza-Vázquez et al., 2000).

Figure 7:
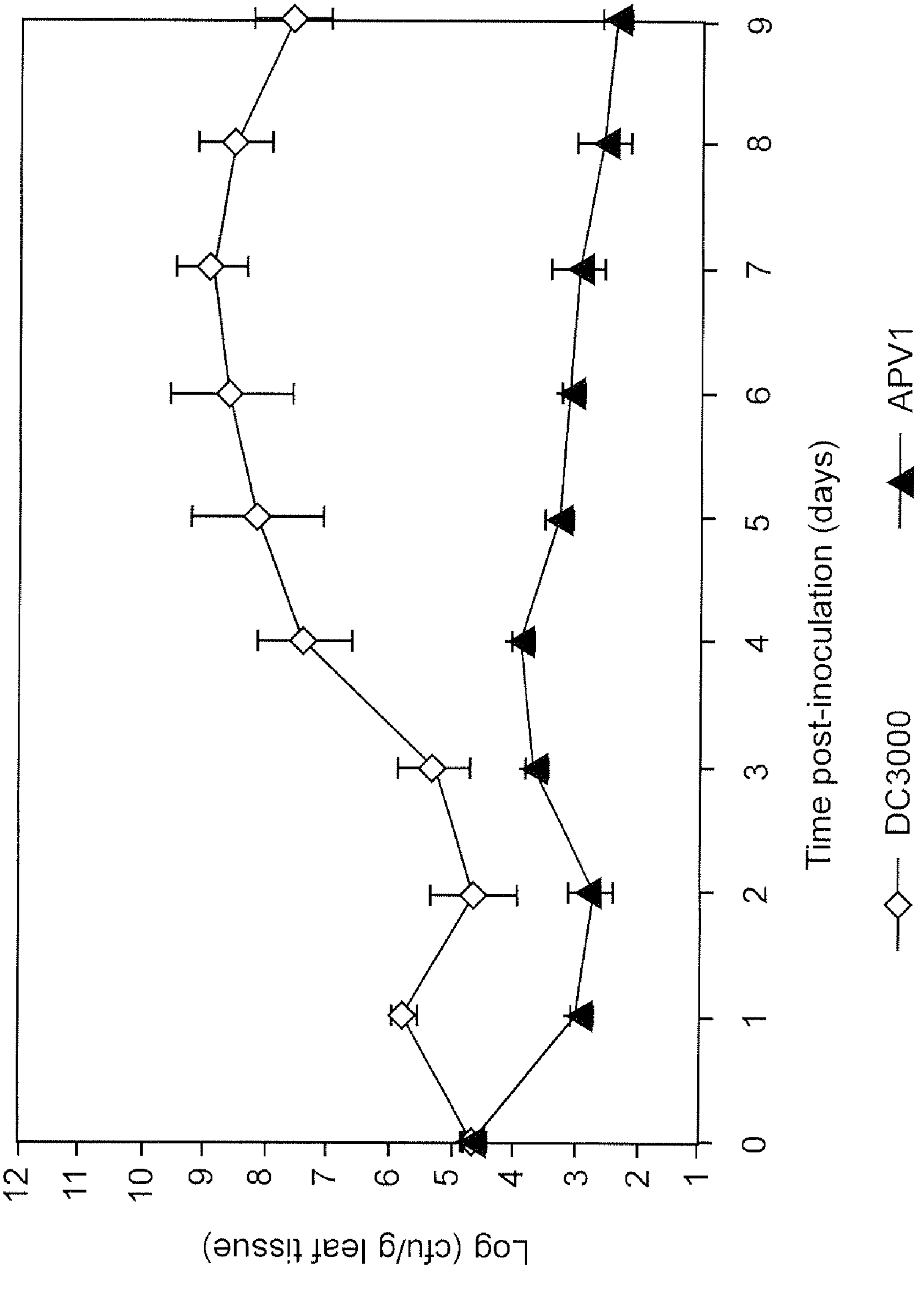
FIG. 7. Growth of *P. syringae* pv. tomato DC3000 (parent strain) and APV1 (strain genetically improved for coronatine production) on tomato. Leaves were inoculated as described above and bacterial populations were monitored using established techniques (Peñaloza-Vázquez et al., 2000).

The results indicated that strain APV1 is severely impaired in its ability to persist and multiply in tomato leaves; for example, the population of APV1 was 10,000-fold lower than the parent strain DC3000 at the end of the sampling period (9 days) (FIG. 7). The impaired pathogenicity (FIG. 6B) and fitness (FIG. 7) of strain APV1 bode well for the registration of this strain for COR production as it will not be classified as a pathogenic strain.

In summary, there are several key advantages for using the genetically improved strain APV1 for COR production: (1) significantly higher yields of COR are obtained with APV1 as compared to the parent strain DC3000; (2) APV1 produces optimal levels of COR at approximately 26° C., a temperature more appropriate for large-scale fermentations; (3) the lag time for optimal COR production by APV1 was decreased (COR is produced earlier in the fermentation than observed for the parent strain); and (4) the modified strain APV1 is nonpathogenic.

REFERENCES FOR EXAMPLE 1

Alexeyev, M. F. (1995) Three kanamycin resistance gene cassettes with different polylinkers. BioTechniques 18: 52-55.

Bender, C. L., Young, S. A., and Mitchell, R. E. (1991) Conservation of plasmid DNA sequences in coronatine-producing pathovars of *Pseudomonas syringae*. Appl. Environ. Microbiol. 57: 993-999.

Burns, J. K., Pozo, L. V., Arias, C.R., Hockema, B., Rangaswamy, V., and Bender, C. L. 2003. Coronatine and abscission in citrus. J. Amer. Soc. Hort. Sci. 128: 309-315.

Ferguson, I., and Mitchell, R. (1985) Stimulation of ethylene production in bean leaf discs by the Pseudomonad phytotoxin coronatine. Plant Physiol. 77: 969-973.

Feys, B., Penfold, C. and Turner, J. (1994) *Arabidopsis* mutants selected for resistance to the phytotoxin coronatine are male sterile, insensitive to methyl jasmonate, and resistant to a bacterial phytotoxin. Plant Cell 6: 751-759.

Hirano, S. S., Charkowski, A. O., Collmer, A., Willis, D. K., and Upper, C. D. (1999) Role of the Hrp type III protein secretion system in growth of *Pseudomonas syringae* pv. *syringae* B728a on host plants in the field. Proc. Natl. Acad. Sci. USA 96: 9851-9856.

Ichihara, A., Shiraishi, K., Sato, H., Sakamura, S., Nishiyama, K., Sakai, R., Furusaki, A., and Matsumoto, T. (1977) The structure of coronatine. J. Am. Chem. Soc. 99: 636-637.

Jin, Q., Thilmony, R., Zwiesler-Vollick, J., and He, S. Y. (2003) Type III protein secretion in *Pseudomonas syringae*. Microbes Infect. 5: 301-310.

Keith, L. M., and Bender, C. L. (1999) AlgT controls alginate production and tolerance to environmental stress in *Pseudomonas syringae*. J. Bacteriol. 181: 7176-7184.

Palmer, D. A., and Bender, C. L. (1993) Effects of environmental and nutritional factors on production of the polyketide phytotoxin coronatine by *Pseudomonas syringae* pv. *glycinea*. Appl. Environ. Microbiol. 59: 1619-1626.

Palmer, D. A., and Bender, C. L. (1995) Ultrastructure of tomato leaf tissue treated with the Pseudomonad phytotoxin coronatine and comparison with methyl jasmonate. Mol. Plant-Microbe Interact. 8: 683-692.

Penaloza-Vazquez, A., Preston, G. M., Collmer, A., and Bender, C. L. (2000) Regulatory interactions between the Hrp type III protein secretion system and coronatine biosynthesis in *Pseudomonas syringae* pv. tomato DC3000. Microbiology 146: 2447-2456.

Rohde, B. H., Pohlack, B., and Ullrich, M. S. (1998) Occurrence of thermoregulation of genes involved in coronatine biosynthesis among various *Pseudomonas syringae* strains. J. Basic Microbiol. 38: 41-50.

Ullrich, M., Penaloza-Vazquez, A., Bailey, A. M., and Bender, C. L. (1995) A modified two-component regulatory system is involved in temperature-dependent biosynthesis of the *Pseudomonas syringae* phytotoxin coronatine. J. Bacteriol. 177: 6160-6169.

Weiler, E. W., T. M. Kutchan, T. Gorba, W. Brodschelm, U. Neisel, and F. Bublitz. 1994. The *Pseudomonas* phytotoxin coronatine mimics octadecanoid signaling molecules of higher plants. FEBS Lett. 345:9-13.

Yu, J., Penaloza-Vazquez, A., Chakrabarty, A. M., and Bender, C. L. (1999) Involvement of the exopolysaccharide alginate in the virulence and epiphytic fitness of *Pseudomonas syringae* pv. *syringae*. Mol. Microbiol. 33: 712-720.

Example 2

Optimization of Coronatine Production in a Genetically Improved Strain of *Pseudomonas syringae*

Coronatine (COR) is a phytohormone produced by several variants of *Pseudomonas syringae* (Bender et al., 1999). Coronatine shares significant structural and functional similarities with jasmonic acid (FIG. 1), its precursor 12-oxophytodienoate, and methyl jasmonate, which are plant growth substances important in octadecanoid signaling (Weiler et al., 1994). Components of the octadecanoid pathway regulate fruit ripening and abscission (Burns, 2002). This is germane to the present invention since COR has properties analogous to octadecanoid signaling molecules and has utility as a selective fruit loosening agent in citrus (Burns et al., 2003) (see also, U.S. Pat. No. 6,511,939 entitled "Coronatine as an Abscission Agent for Citrus," the disclosure of which is incorporated herein by reference). Several factors have limited the ability to utilize COR as an abscission agent including: (i) the low yields obtained from the fermentation; (ii) a requirement of 18° C. for optimal production; and (iii) a long incubation period (7 days) for optimal levels of COR (Palmer and Bender, 1993; Burns et al., 2003). In this Example, conditions for optimizing the yield of COR in the fermentation of the genetically modified strain, APV1 (see Example 1) are described.

This Example 2 describes conditions for optimal production of COR by the genetically improved strain, APV1. *P. syringae* strain APV1 produces substantially higher levels of COR than the parent strain, DC3000, and production of COR by APV1 is optimal at 26° C., a temperature more favorable for large-scale fermentation than 18° C., which is the optimal temperature for DC3000. This and other aspects of the invention are elaborated in one or more of the embodiments described below.

One embodiment of the invention presents the results of using immobilized cells of *Pseudomonas* to produce COR. Immobilization of bacterial cells on a matrix facilitates membrane stabilization, which protects cells and improves viability. In these experiments, the yield of COR is compared for freely suspended cells of APV1 and cells of APV1 entrapped in various matrices. Another embodiment of the invention provides a method to immobilize *Pseudomonas* cells in two different matrices: (1) calcium alginate and (2) Cytoline™ 2; the latter is a novel microcarrier consisting of polyethylene and silica (Amersham Biosciences). The invention describes the use of immobilized cells of APV1 to produce COR at 26° C. within a 24 h incubation period. The end result is a method to produce COR in a cost-effective manner.

Use of immobilized cells of *Pseudomonas* to produce COR. The literature on the use of immobilized cells for the production of secondary metabolites is considerable (Banerjee et al., 2006; Shan et al., 2003; Tse and Yu, 2003). Immobilization of bacterial cells on a matrix is known to facilitate membrane stabilization, which protects cells and improves viability (Hann et al. 2002; Sharanagouda and Karegoudar, 2002). Cells at different stages (dead, resting/living, and actively growing) have been successfully entrapped in various matrices (Sharanagouda and Karegoudar, 2002; Tse and Yu, 2003; Wang et al., 2002; Yamamoto et al. 1980). As a result, reactions based on immobilized cell preparations offer several advantages compared to conventional fermentation including: (i) higher reaction rates due to increased cell densities; (ii) higher specific product yield; (iii) continuous operation; (iv) reduced costs; and (v) ease of scale-up for commercial production (Banerjee et al., 2006; Diaz et al., 2002; Wang et al., 2002). Table 1 provides examples where immobilized *Pseudomonas* spp. have been used to provide a commercially important compound or process.

TABLE 1

Production of various products or processes using different immobilization matrices and *Pseudomonas* spp.

| *Pseudomonas* strains | Matrix | Desired Product or Process | References |
|---|---|---|---|
| GM3 | Porous glass beads and solid PVA particles | Biodegradation of Azo Compounds | Tse and Yu, 2003 |
| ZD8 | Wood chips | Filtration of air pollutants (Biodegradation of rapeseed oil smoke) | Miao et al., 2005 |
| TCP114 | Calcium alginate | Degradation of 2,4,6-trichlorophenol | Bae et al., 1997 |
| NGK1 | Calcium alginate | Degradation of 2-methylnaphthalene | Sharanagouda & Karegoudar, 2002 |
| M285 | Diatomaceous earth beads | Degradation of 3,5,6-trichloro-2-pyridinol from industrial wastewater | Feng et al, 1997 |
| *P. dacunhae* | Carrageenan | Production of L-alanine | Yamamoto et al., 1980 |

The support matrix for immobilization must have an adaptable pore capacity and diameter to avoid loss of cells and provide optimal conditions for transport of substrates and the elimination of metabolites (Zohar-Perez et al., 2003; Wang et al. 2002). Consequently, there is no universal optimal support system because requirements for particular applications differ (Brodelius and Mosbach, 1987). The choice of the proper carrier or support is governed by factors such as cost, ease of preparation, mechanical stability, biocompatibility, and resistance to biodegradation (Brodelius and Mosbach, 1987).

Figure 8:
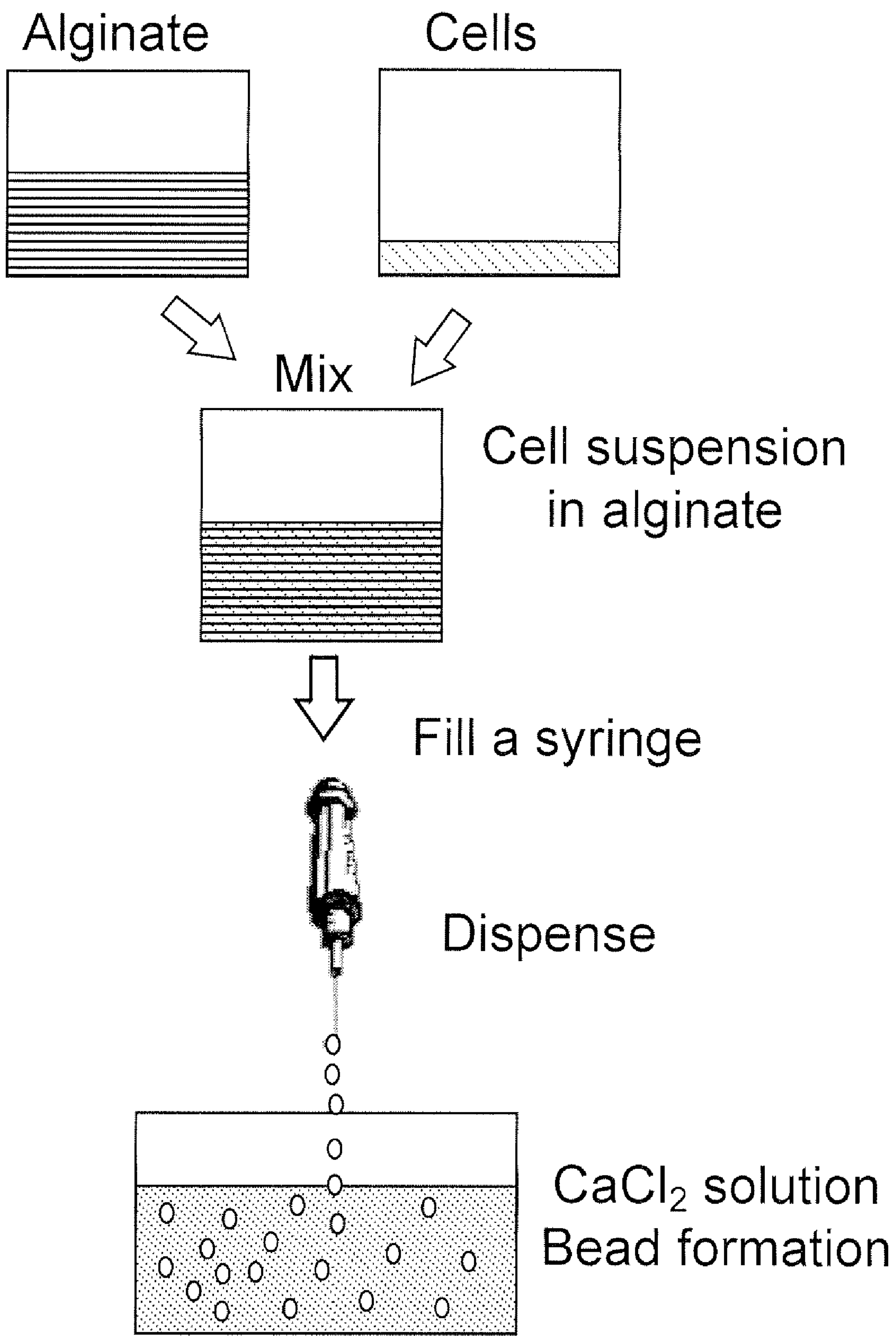
FIG. 8. Immobilization of *P. syringae* in calcium alginate. Sodium alginate (3%-5%) is dissolved in distilled water and mixed with *Pseudomonas* cells. The suspension is then dispensed dropwise into a solution of 0.1 M calcium chloride. On a small scale, this can be accomplished using a syringe (Bucke, 1987).

Experimental approach. Two methods of cell immobilization were screened. Cells of *P. syringae* strain APV1 (the genetically improved strain) were entrapped in two different support matrices, and the amounts of COR produced were compared with the levels produced by freely suspended cells in batch fermentation. For both immobilized and free cells, the initial cell density was $OD_{600}$=1.37, and COR production was calculated as the volumetric rate of production (COR g/L/h) after each cycle of COR production (e.g. 24 h). The two support matrices tested were calcium alginate and Cytoline™ 2, which is a microcarrier consisting of polyethylene and silica (Amersham Biosciences). Calcium alginate was prepared as described previously (Bucke, 1987; see FIG. 8), and Cytoline 2 was prepared as described by the manufacturer (Amersham). COR production was evaluated in repeated batch fermentations for free and immobilized cells of strain APV1. After removing the exhausted medium, the cells were washed with sterile water, and 30 ml of fresh culture medium was added for the next cycle of fermentation (1 cycle=24 h).

Figure 9:
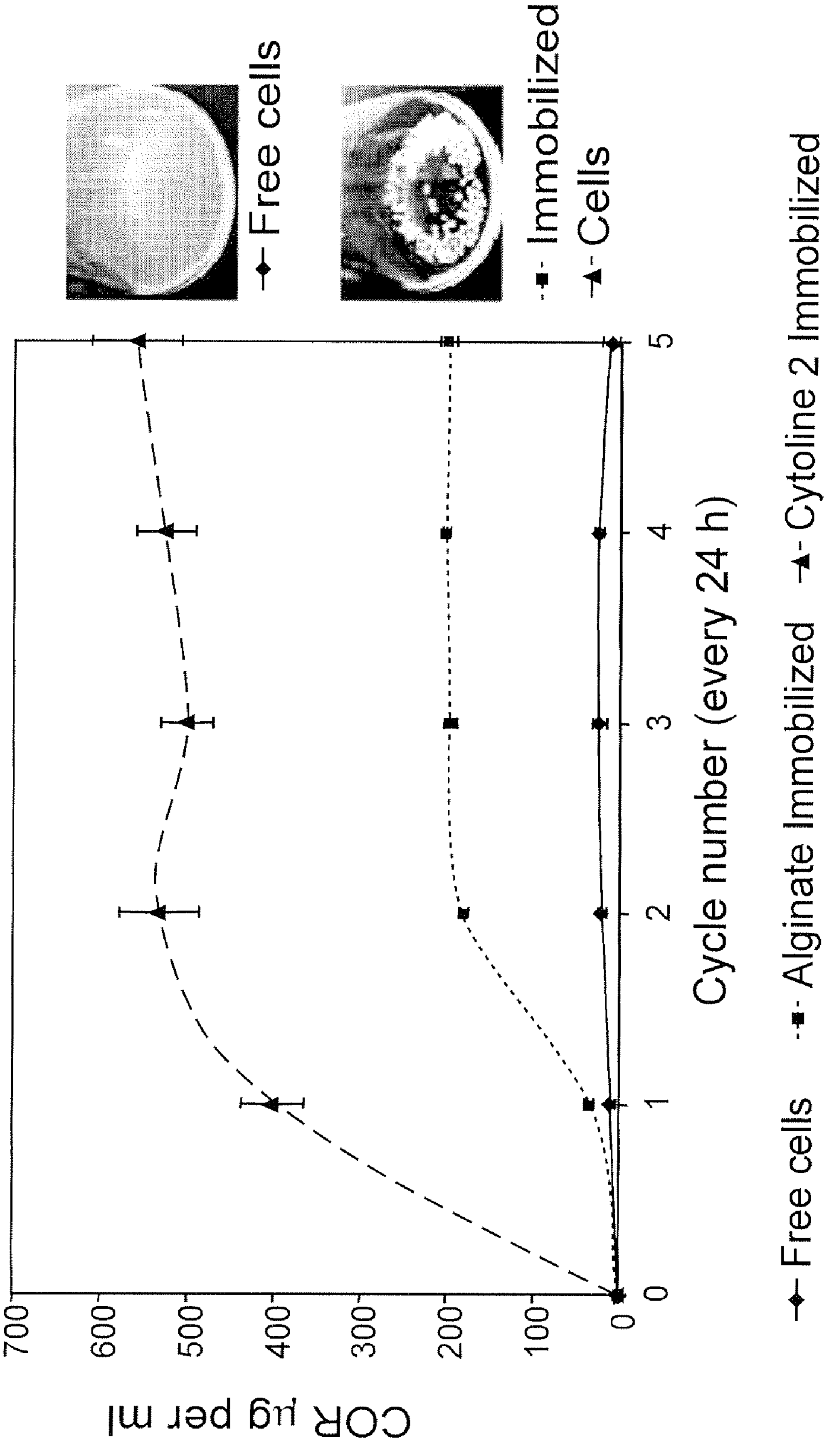
FIG. 9. Semicontinuous batch fermentation of *Pseudomonas* strain APV1. COR production is shown for freely-suspended and immobilized cells of APV1. Bacteria were incubated in HSS medium at 25° C., and the medium was replaced every 24 h.

Result. After the fifth cycle, COR production was 559, 200, and 12 μg/ml for Cytoline™ 2-immobilized cells, calcium alginate-immobilized cells, and free cells of APV1, respectively (FIG. 9). These results indicate that COR yields are substantially higher when immobilized cells of *P. syringae* are used. Furthermore, Cytoline™ 2 was superior to calcium alginate as an immobilization matrix and did not show any decomposition during repeated cycles of fermentation. Decomposition was a problem observed with calcium alginate, possibly because *P. syringae* produces alginate lyase, an enzyme that degrades alginate.

In summary, a procedure for optimal production of COR by the genetically improved strain APV1 has been identified. Using Cytoline™ 2 as an immobilization matrix, COR production by APV1 was increased to 400 μg/ml at 24 h. This is approximately 100-fold higher than the amount of COR synthesized by free cells of APV1 (FIG. 9). The use of immobilized cells and the implementation of strain APV1 have made it possible to produce large amounts of COR with minimal lag time, thus increasing opportunities to bring the compound to market as an abscission aid.

REFERENCES FOR EXAMPLE 2

Bae, H. S., Lee, J. M., and Lee, S. T. (1997) Biodegradation of the mixture of 2,4,6-trichlorophenol, 4-chlorophenol, and phenol by a defined mixed culture. J. Gen. Appl. Microbiol. 43: 97-103.

Banerjee, A., Kaul, P., and Banerjee, U. C. (2006) Enhancing the catalytic potential of nitrilase from *Pseudomonas putida* for stereoselective nitrile hydrolysis. Appl. Microbiol. Biotechnol. 72:77-87.

Bender, C. L., Alarcon-Chaidez, F., and Gross, D.C. (1999) *Pseudomonas syringae* phytotoxins: mode of action, regulation, and biosynthesis by peptide and polyketide synthetases. Microbiol. Mol. Biol. Rev. 63: 266-292.

Brodelius, P., and K. Mosbach. (1987) Overview of immobilization techniques for cells/organelles. Meth. Enzymol. 135:173-175.

Bucke, C. 1987. Cell immobilization in calcium alginate. In Immobilization Techniques for cells/organelles. Meth. Enzymol. 135:175-189.

Burns, J. K. (2002) Using molecular biology tools to identify abscission materials for citrus. HortScience 37: 459-464.

Burns, J. K., Pozo, L. V., Arias, C.R., Hockema, B., Rangaswamy, V., and Bender, C. L. 2003. Coronatine and abscission in citrus. J. Amer. Soc. Hort. Sci. 128: 309-315.

Diaz, M. P., Boyd, K. G., Grigson, S. J. W. and Burgess, J. G. (2002) Biodegradation of crude oil across a wide range of salinities by an extremely halotolerant bacterial consortium MPD-M, immobilized onto polypropylene fibers. Biotechnol. Bioeng. 79:145-153.

Feng, Y., Racke, K. D., and Bollag, J. M. (1997) Use of immobilized bacteria to treat industrial wastewater containing a chlorinated pyridinol. Appl. Microbiol. Biotechnol. 47: 73-77.

Hann, E. C., A. E. Sigmund, S. M. Hennessey, J. E. Gavagan, D. R. Short, A. Ben-Bassat, S. Chauhan, R. D. Fallon, M. S. Payne, and R. DiCosimo. (2002) Optimization of an immobilized-cell biocatalyst for production of 4-cyanopentanoic acid. Org. Process Res. Develop. 6:492-496.

Ichihara, A., Shiraishi, K., Sato, H., Sakamura, S., Nishiyama, K., Sakai, R., Furusaki, A., and Matsumoto, T. (1977) The structure of coronatine. J. Am. Chem. Soc. 99: 636-637.

Miao, J. Y., Zheng, L. Y., and Guo, X. F. (2005) Restaurant emissions removal by a biofilter with immobilized bacteria. J. Zhejiang Univ. Sci. B 6: 433-437.

Palmer, D. A., and Bender, C. L. (1993) Effects of environmental and nutritional factors on production of the polyketide phytotoxin coronatine by *Pseudomonas syringae* pv. *glycinea*. Appl. Environ. Microbiol. 59: 1619-1626.

Shan, G. B., Xing, J. M., Luo, M. F., Liu, H. Z., and Chen, J. Y. (2003) Immobilization of *Pseudomonas delafieldii* with magnetic polyvinyl alcohol beads and its application in biodesulfurization. Biotechnol. Lett. 25: 1977-1981.

Sharanagouda, U. and T. B. Karegoudar. (2002) Degradation of 2-methylnaphthalene by free and immobilized cells. World J. Microbiol. Biotechnol. 18:225-230.

Tse, S. W., and Yu, J. (2003) Adsorptive immobilization of a *Pseudomonas* strain on solid carriers for augmented decolourization in a chemostat bioreactor. Biofouling 19: 223-233.

Vorlop, K. D., and J. Klein. (1987) Entrapment of microbial cells in chitosan. Meth. Enzymol. 135:259-268.

Wang, H., S. Liu, and Y. Wang. (2002) Alkaline protease production by immobilized growing cells of *Serratia marcescens* with interpolymer complex of P(TM-co-Aam)/PAA. J. Appl. Polymer Sci. 84:178-183.

Weiler, E. W., T. M. Kutchan, T. Gorba, W. Brodschelm, U. Niesel, and F. Bublitz (1994) The *Pseudomonas* phytotoxin coronatine mimics octadecanoid signalling molecules of higher plants. FEBS Lett 345:9-13.

Yamamoto, K., T. Tosa, and I. Chibata. (1980) Continuous production of L-alanine using *Pseudomonas dacunhae* immobilized with carrageennan. Biotechnol. Bioeng. 22:2045

Zohar-Perez, C., Chemin, L., Chet, I., and Nussinovitch, A. (2003) Structure of dried cellular alginate matrix containing fillers provides extra protection for microorganisms against UVC radiation. Radiat. Res. 160:198-204.

In view of the above, it will be seen that the several objectives of the invention are achieved and other advantageous results attained. As various changes could be made without departing from the scope of the invention, it is intended that all matter contained in the above description or shown in the accompanying drawings shall be interpreted as illustrative and not in a limiting sense.

We claim:

1. A stable genetically engineered bacterial strain that overproduces coronatine, wherein said bacterial strain is a Gram negative strain, and wherein said stable bacterial strain contains a genetically engineered mutation of a type III secretion system gene resulting from insertion of a cassette that does not contain genes for transposition.

2. The stable genetically engineered bacterial strain of claim 1, wherein said stable bacterial strain is a *Pseudornonas syringae* bacterial strain.

3. The stable genetically engineered bacterial strain of claim 1, wherein said genetically engineered mutation is an insertion of a stable genetic element.

4. The stable genetically engineered bacterial strain of claim 3, wherein said stable genetic element is an antibiotic resistance cassette.

5. The stable genetically engineered bacterial strain of claim 4, wherein the antibiotic resistance cassette is from the aminoglycoside phosphotransferase class of antibiotic resistance genes.

6. The stable genetically engineered bacterial strain of claim 4, wherein said antibiotic resistance cassette is a kanamycin resistance ($Km^r$) cassette.

7. The stable genetically engineered bacterial strain of claim 1, wherein said type III secretion system gene is hrcC.

8. The stable genetically engineered bacterial strain of claim 7, wherein said stable genetic element is inserted into an SphI cleavage site within the hrcC gene.

9. The stable genetically engineered bacterial strain of claim 1, wherein said stable genetically engineered bacterial strain is non-pathogenic.

10. The stable genetically engineered bacterial strain of claim 1, wherein said stable genetically engineered bacterial strain produces optimal levels of coronatine at 26° C.

11. A stable genetically engineered bacterial strain that overproduces coronatine, wherein said stable genetically engineered bacterial strain is a *Pseudomonas syringae* bacterial strain, and wherein said stable bacterial strain contains a genetically engineered mutation of a type III secretion system gene resulting from insertion of a cassette that does not contain genes for transposition.

12. A method of producing coronatine, comprising the steps of culturing in a culture medium a stable genetically engineered bacterial strain that overproduces coronatine, wherein said bacterial strain is a Gram negative strain, and wherein said stable bacterial strain contains a genetically engineered mutation of a type III secretion system gene resulting from insertion of a cassette that does not contain genes for transposition, and removing coronatine produced by said stable genetically engineered bacterial strain in said culture medium.

13. The method of claim 12, wherein said stable genetically engineered bacterial strain is immobilized on a matrix in said culture medium.

14. The method of claim 13, wherein said stable genetically engineered bacterial strain is immobilized on Cytoline™ as a matrix.

15. The method of claim 12, wherein said stable genetically engineered bacterial strain is a *Pseudomonas syringae* bacterial strain.

16. The method of claim 12, wherein said genetically engineered mutation is an insertion of a stable genetic element.

17. The method of claim 16, wherein said stable genetic element is an antibiotic resistance cassette.

18. The method of claim 17, wherein said antibiotic resistance cassette is a kanamycin resistance ($Km^{\sim}$) cassette.

19. The method of claim 12, wherein said type III secretion system gene is hrcC.

20. The method of claim 19, wherein said stable genetic element is inserted into an SphI cleavage site within the hrcC gene.

21. The method of claim 12, wherein said stable genetically engineered bacterial strain is non-pathogenic.

22. The method of claim 12, wherein said step of culturing is carried out at 20° C. to 30° C.

23. The method of claim 12, wherein said stable genetically engineered bacterial strain produces optimal levels of coronatine at 26° C.

24. A matrix comprising a stable genetically engineered Gram negative bacterial strain that overproduces coronatine immobilized thereon, wherein said stable bacterial strain contains a genetically engineered mutation of a type III secretion system gene resulting from insertion of a cassette that does not contain genes for transposition.

25. The matrix of claim 24, wherein said matrix comprises polyethylene weighted with silica.

* * * * *

SEQUENCE LISTING

```
<160> NUMBER OF SEQ ID NOS: 3

<210> SEQ ID NO 1
<211> LENGTH: 795
<212> TYPE: DNA
<213> ORGANISM: Artificial
```

-continued

<220> FEATURE:
<223> OTHER INFORMATION: sequence from synthetic plasmid encoding kanamycin resistance

<400> SEQUENCE: 1
atgattgaac aagatggatt gcacgcaggt tctccggccg cttgggtgga gaggctattc 60
ggctatgact gggcacaaca gacaatcggc tgctctgatg ccgccgtgtt ccggctgtca 120
gcgcaggggc gcccggttct ttttgtcaag accgacctgt ccggtgccct gaatgaactc 180
caagacgagg cagcgcggct atcgtggctg gccacgacgg gcgttccttg cgcagctgtg 240
ctcgacgttg tcactgaagc gggaagggac tggctgctat tgggcgaagt gccggggcag 300
gatctcctgt catctcacct tgctcctgcc gagaaagtat ccatcatggc tgatgcaatg 360
cggcggctgc atacgcttga tccggctacc tgcccattcg accaccaagc gaaacatcgc 420
atcgagcgag cacgtactcg gatggaagcc ggtcttgtcg atcaggatga tctggacgaa 480
gagcatcagg ggctcgcgcc agccgaactg ttcgccaggc tcaaggcgcg gatgcccgac 540
ggcgaggatc tcgtcgtgac ccatggcgat gcctgcttgc cgaatatcat ggtggaaaat 600
ggccgctttt ctggattcat cgactgtggc cggctgggtg tggcggaccg ctatcaggac 660
atagcgttgg ctacccgtga tattgctgaa gagcttggcg gcgaatgggc tgaccgcttc 720
ctcgtgcttt acggtatcgc cgctcccgat tcgcagcgca tcgccttcta tcgccttctt 780
gacgagttct tctga 795

<210> SEQ ID NO 2
<211> LENGTH: 1941
<212> TYPE: DNA
<213> ORGANISM: Pseudomonas syringae

<400> SEQUENCE: 2
atgtcgctcg acatgtcgcc tgtccagggc aagctcgatg gccgtattcg tgctcagaac 60
cctgaagagt ttcttgagcg gctgagtcag gaataccact tccagtggtt cgtctataac 120
gacacgctgt atgtcagccc ttccagcgag cacacctcgg cgcgcatcga agtctcgccg 180
gatgcggtgg acgacctgca aacggcgctg accgatgtcg gtctgctgga caagcgtttt 240
ggctggggct cgctgcctga cgaaggcgtg gttctggttc gtggtccggc caaatacgtg 300
gagtttgtgc gcgactacag caagaaagtc gaaaagcccg acgagaaggc cgacaagcaa 360
gatgttgtcg tgctgccact caaatacgcc aacgcggctg atcggactat tcgctaccgt 420
gaccagcagt tagtggtggc cggtgtcgcc agtattcttc aagagctgct ggaaagccgt 480
tcgcgtggcg aaagcattga cagcgtgaac ctgttgccgg ggcagggcag cagtgttgcc 540
aacagcacag gtgtcgcggc cgccggcctg ccttacaacc tgggctccaa tggtatcgat 600
acgggagcac tgcaacaggg cattgaccgc gtattgaact tcaacagcaa aaaaactgcc 660
aagggtcatg cctcaggcaa ggcaaatatc cgcgtaagcg ctgatgtgcg taacaactcc 720
gtattgattt acgacctgcc agagcgcaag gccatgtacc agaaactggt caaggagctg 780
gacgttccgc gcaacctgat cgaaatcgat gcggtcattc tcgacatcga ccgcaatgaa 840
ctggctgaac tgtccagtcg ctggaatttc aatgccggca gcgtcggagg tggtgccaac 900
ctgtttgatg caggcaccag ttcaacgttg ttcttgcaga acgccagcaa gttttctgcc 960
gaattgcatg cgcttgaagg caatggttct gcgtcagtca tcggcaaccc gtcgatcctg 1020
accctggaga atcagcctgc agtgatcgac ctcagtcgca ccgaatacct gacggccact 1080
tccgagcggg ccgctgacat tctgcccatc acggcgggca ccagccttca agtgattccg 1140

-continued

```
cgttcgctgg acaacgatgg caagcctcag gtgcaaatga tcgtggacat cgaggatggc   1200

cagatcgatg tgtcgacgat caatgacacc caacccagtg tgcgccgagg caatgtcagc   1260

acccaggcgg tgattgccga gcacggctcg ctggtcatcg gcggcttcca cggtctggaa   1320

gccaatgaca ggattcacaa gatcccgctg ttgggcgaca ttccctatat cggcaagctg   1380

ctgttccagt cccgcagtcg cgaactgagt cagcgcgagc ggctgttcat tctgacccct   1440

cgactgatcg gcgatcaggt caatccagca cgctatgtac agaacggcaa cccccatgac   1500

gtcgatgacc agatgaagaa aatcaaggaa cgacgtgacg gaggcgagct gccaacgcgg   1560

ggcgacatcc agaaagtctt tacccaaatg atcgacggcg ccgcccccgga aggcctgcgc   1620

gctggccaga ccctgccctt tgaaaccgat agtctgtgtg atccgggcga aggtctgacg   1680

cttgatgggc agcgctcgca gtggttcgtc aaaaaagact ggggtgttgc tgtggtggtt   1740

gcgcgtaaca acacggacaa gccggtacgt atcgacgaaa gccgatgcgg cggtcgctgg   1800

gtcatcggcg ttgcggcctg gcctcatgca tggctgcagc cgggtgaaga aagtgaggtg   1860

tacatcgctg tgcgccagcc gcagatatct aaaatggcca aagaaagcag gccgtcactg   1920

ctccggggag cgaaaccatg a                                             1941
```

```
<210> SEQ ID NO 3
<211> LENGTH: 3126
<212> TYPE: DNA
<213> ORGANISM: Artificial
<220> FEATURE:
<223> OTHER INFORMATION: P. syringae hrcC gene disrupted by kanamycin resistance gene at
      SphI site

<400> SEQUENCE: 3
```

```
atgtcgctcg acatgtcgcc tgtccagggc aagctcgatg gccgtattcg tgctcagaac     60

cctgaagagt ttcttgagcg gctgagtcag gaataccact tccagtggtt cgtctataac    120

gacacgctgt atgtcagccc ttccagcgag cacacctcgg cgcgcatcga agtctcgccg    180

gatgcggtgg acgacctgca aacggcgctg accgatgtcg gtctgctgga caagcgtttt    240

ggctggggct cgctgcctga cgaaggcgtg gttctggttc gtggtccggc caaatacgtg    300

gagtttgtgc gcgactacag caagaaagtc gaaaagcccg acgagaaggc cgacaagcaa    360

gatgttgtcg tgctgccact caaatacgcc aacgcggctg atcggactat tcgctaccgt    420

gaccagcagt tagtggtggc cggtgtcgcc agtattcttc aagagctgct ggaaagccgt    480

tcgcgtggcg aaagcattga cagcgtgaac ctgttgccgg ggcagggcag cagtgttgcc    540

aacagcacag gtgtcgcggc cgccggcctg ccttacaacc tgggctccaa tggtatcgat    600

acgggagcac tgcaacaggg cattgaccgc gtattgaact tcaacagcaa aaaaactgcc    660

aagggtcatg cctcaggcaa ggcaaatatc cgcgtaagcg ctgatgtgcg taacaactcc    720

gtattgattt acgacctgcc agagcgcaag gccatgtacc agaaactggt caaggagctg    780

gacgttccgc gcaacctgat cgaaatcgat gcggtcattc tcgacatcga ccgcaatgaa    840

ctggctgaac tgtccagtcg ctggaatttc aatgccggca gcgtcggagg tggtgccaac    900

ctgtttgatg caggcaccag ttcaacgttg ttcttgcaga acgccagcaa gttttctgcc    960

gaattgcatg cctgcagtcg actctagagg atcccgggta ccgagctcga attcgctagc   1020
```

-continued

```
ttcacgctgc cgcaagcact cagggcgcaa gggctgctaa aggaagcgga acacgtagaa   1080
agccagtccg cagaaacggt gctgaccccg gatgaatgtc agctactggg ctatctggac   1140
aagggaaaac gcaagcgcaa agagaaagca ggtagcttgc agtgggctta catggcgata   1200
gctagactgg gcggttttat ggacagcaag cgaaccggaa ttgccagctg gggcgccctc   1260
tggtaaggtt gggaagccct gcaaagtaaa ctggatggct ttcttgccgc caaggatctg   1320
atggcgcagg ggatcaagat ctgatcaaga gacaggatga ggatcgtttc gcatgattga   1380
acaagatgga ttgcacgcag gttctccggc cgcttgggtg gagaggctat tcggctatga   1440
ctgggcacaa cagacaatcg gctgctctga tgccgccgtg ttccggctgt cagcgcaggg   1500
gcgcccggtt ctttttgtca agaccgacct gtccggtgcc ctgaatgaac tccaagacga   1560
ggcagcgcgg ctatcgtggc tggccacgac gggcgttcct tgcgcagctg tgctcgacgt   1620
tgtcactgaa gcgggaaggg actggctgct attgggcgaa gtgccggggc aggatctcct   1680
gtcatctcac cttgctcctg ccgagaaagt atccatcatg gctgatgcaa tgcggcggct   1740
gcatacgctt gatccggcta cctgcccatt cgaccaccaa gcgaaacatc gcatcgagcg   1800
agcacgtact cggatggaag ccggtcttgt cgatcaggat gatctggacg aagagcatca   1860
ggggctcgcg ccagccgaac tgttcgccag gctcaaggcg cggatgcccg acggcgagga   1920
tctcgtcgtg acccatggcg atgcctgctt gccgaatatc atggtggaaa atggccgctt   1980
ttctggattc atcgactgtg gccggctggg tgtggcggac cgctatcagg acatagcgtt   2040
ggctacccgt gatattgctg aagagcttgg cggcgaatgg gctgaccgct tcctcgtgct   2100
ttacggtatc gccgctcccg attcgcagcg catcgccttc tatcgccttc ttgacgagtt   2160
cttctgagcg ggactctggg gttcgaattc gagctcggta cccggggatc cgtcgactgc   2220
agcatgcgct tgaaggcaat ggttctgcgt cagtcatcgg caacccgtcg atcctgaccc   2280
tggagaatca gcctgcagtg atcgacctca gtcgcaccga atacctgacg gccacttccg   2340
agcgggccgc tgacattctg cccatcacgg cgggcaccag ccttcaagtg attccgcgtt   2400
cgctggacaa cgatggcaag cctcaggtgc aaatgatcgt ggacatcgag gatggccaga   2460
tcgatgtgtc gacgatcaat gacacccaac ccagtgtgcg ccgaggcaat gtcagcaccc   2520
aggcggtgat tgccgagcac ggctcgctgg tcatcggcgg cttccacggt ctggaagcca   2580
atgacaggat tcacaagatc ccgctgttgg gcgacattcc ctatatcggc aagctgctgt   2640
tccagtcccg cagtcgcgaa ctgagtcagc gcgagcggct gttcattctg accccctcgac   2700
tgatcggcga tcaggtcaat ccagcacgct atgtacagaa cggcaacccc catgacgtcg   2760
atgaccagat gaagaaaatc aaggaacgac gtgacggagg cgagctgcca acgcggggcg   2820
acatccagaa agtctttacc caaatgatcg acggcgccgc cccggaaggc ctgcgcgctg   2880
gccagaccct gccctttgaa accgatagtc tgtgtgatcc gggcgaaggt ctgacgcttg   2940
atgggcagcg ctcgcagtgg ttcgtcaaaa aagactgggg tgttgctgtg gtggttgcgc   3000
gtaacaacac ggacaagccg gtacgtatcg acgaaagccg atgcggcggt cgctgggtca   3060
tcggcgttgc ggcctggcct catgcatggc tgcagccggg tgaagaaagt gaggtgtaca   3120
tcgctg                                                              3126
```